US010111881B2

(12) United States Patent
Davey et al.

(10) Patent No.: US 10,111,881 B2
(45) Date of Patent: Oct. 30, 2018

(54) INHIBITORS OF MACROPINOCYTOSIS IN PREVENTION AND TREATMENT OF DISEASE

(71) Applicant: Texas Biomedical Research Institute, San Antonio, TX (US)

(72) Inventors: Robert Andrew Davey, Helotes, TX (US); Manu Anantpadma, San Antonio, TX (US)

(73) Assignee: Texas Biomedical Research Institute, San Antonio, TX (US)

( * ) Notice: Subject to any disclaimer, the term of this patent is extended or adjusted under 35 U.S.C. 154(b) by 0 days.

(21) Appl. No.: 15/479,032

(22) Filed: Apr. 4, 2017

(65) Prior Publication Data

US 2018/0161333 A1 Jun. 14, 2018

Related U.S. Application Data

(60) Provisional application No. 62/318,092, filed on Apr. 4, 2016.

(51) Int. Cl.
*A61K 31/5377* (2006.01)
*A61P 31/12* (2006.01)
*A61K 31/4155* (2006.01)
*C07D 409/14* (2006.01)
*C07D 413/12* (2006.01)

(52) U.S. Cl.
CPC ...... *A61K 31/5377* (2013.01); *A61K 31/4155* (2013.01); *A61P 31/12* (2018.01); *C07D 409/14* (2013.01); *C07D 413/12* (2013.01)

(58) Field of Classification Search
USPC .................................................. 514/231.5
See application file for complete search history.

(56) References Cited

PUBLICATIONS

ChemSpider teaches General formula (I).*
CAS No. 958948-76-0 (which is General formula II).*
Aleksandrowicz, et al., Ebola virus enters host cells by macropinocytosis and clathrin-mediated endocytosis; The Journal of Infectious Diseases; 2011; vol. 204 Suppl 3 , S957-967.
Bajusz, et al., "Why is Tanimoto index an appropriate choice for fingerprint-based similarity calculations?" Journal of Cheminformatics; 2015; vol. 7, p. 20.
Barrette, et al., Current perspectives on the phylogeny of Filoviridae; Infection, Genetics and Evolution; Journal of Molecular Epidemiology and Evolutionary Genetics in Infectious Diseases; vol. 11; pp. 1514-1519.
Basu, et al., High-Throughput Screening of Viral Entry Inhibitors Using Pseudotyped Virus; Current Protocols in Pharmacology; Dec. 2010; Chapter 13 , Unit 13B 13.
Basu, et al., Identification of a Small-Molecule Entry Inhibitor for Filoviruses; Journal of Virology; 2011; vol. 85, pp. 3106-3119.
Bukreyev, et al., Discussions and Decisions of the 2012-2014 International Committee on Taxonomy of Viruses (ICTV) Filoviridae Study Group; 2014; Archives of Virology; pp. 821-830; vol. 159, No. 4.
Carette, et al., Ebola virus entry requires the cholesterol transporter Niemann-Pick Cl; Nature; 2011; vol. 477, pp. 340-343.
Carpenter, et al, CellProfiler: image analysis software for identifying and quantifying cell phenotypes; Genome Biology; 2006; vol. 7, R100.
Chandran, et al., Endosomal Proteolysis of the Ebola Virus Glycoprotein is Necessary for Infection; Science; 2005; vol. 308, pp. 643-1645.
Chen, et al., High-Efficiency Transformation of Mammalian Cells by Plasmid DNA, Molecular and Cellular Biology; Aug. 1987; vol. 7; pp. 2745-2752.
Warren, et al., Protection against filovirus diseases by a novel broadspectrum nucleoside analogue BCX4430; Nature; 2014; vol. 508, pp. 402-405.
Cheng, et al. Inhibition of Ebola and Marburg Virus Entry by G Protein-Coupled Receptor Antagonists; Journal of Virology; 2015; vol. 89, pp. 9932-9938.
Chung, et al., Discovery of a Novel Compound with Anti-Venezuelan Equine Encephalitis Virus Activity That Targets Ihe Nonstructural Protein 2; PLoS Pathogens; 2014; vol. 10 , e1004213.
Cote, et al., Small molecule inhibitors reveal Niemann-Pick C1 is essential for Ebolavirus infection; Nature; 2011; vol. 477, vol. 344-348.
Dube, et al. The Primed Ebolavirus Glycoprotein (19-Kilodalton GP1,2): Sequence and Residues Critical for Host Cell Binding; Journal of Virology; 2009; vol. 83, pp. 2883-2891.
Ebihara, et al., In Vitro and In Vivo Characterization of Recombinant Ebola Viruses Expressing Enhanced Green Fluorescent Protein; The Journal of Infectious Diseases; 2007; 196 Suppl 2, S313-322.
Fuss, et al., Isolation of Whole Mononuclear Cells from Peripheral Blood and Cord Blood; Current Protocols in Immunology; Published online in Wiley Interscience (www.interscience.wiley.com); Apr. 2009; Chapter 7, Unit 7.1.1-7.1.8.
Garrison, et al., The cyanobacterial lectin scytovirin displays potent in vitro and in vivo activity against Zaire Ebola virus; Antiviral Research; Dec. 1, 2014; vol. 112, pp. 1-7.
Gnirss, et al., Cathepsins B and L activate Ebola but not Marburg virus glycoproteins for efficient entry into cell lines and macrophages independent of TMPRSS2 expression; Virology; 2012; vol. 424, pp. 3-10.
Hartman, et al., Ebola and Marburg Hemorrhagic Fever; Clinics in Laboratory Medicine; 2010; vol. 30, pp. 161-177.
Heald, et al., Safety and pharmacokinetic profiles of phosphorodiamidate morpholino oligomers with activity against Ebola virus and Marburg virus: Results of two single-ascending-dose studies; 2014; Antimicrobial Agents and Chemotherapy; vol. 58,6639-6647.
Hu, et al., The endosomal-lysosomal system: from acidification and cargo sorting to neurodegeneration; Translational Neurodegeneration; 2015; vol. 4, No. 18.

(Continued)

*Primary Examiner* — Kathrien Ann Cruz
(74) *Attorney, Agent, or Firm* — Bracewell LLP; Karthika Perumal

(57) ABSTRACT

Described herein are pharmaceutical compositions capable of inhibiting vesicle formation and methods of treatment or prophylactic administration of these pharmaceutical compositions to treat pathogenic infections.

2 Claims, 22 Drawing Sheets
(8 of 22 Drawing Sheet(s) Filed in Color)

(56) References Cited

PUBLICATIONS

Hunt, et al., Filovirus Entry: A Novelty in the Viral Fusion World; Viruses; 2012; vol. 4, pp. 258-275.

In, et al., Serine Protease EspP from Enterohemorrhagic *Escherichia coli* is Sufficient to Induce Shiga Toxin Macropinocytosis in Intestinal Epithelium; PloS one; 2013; vol. 8, e69196.

Johansen, et al., A screen of approved drugs and molecular probes identities therapeutics with anti-Ebola virus activity, Science Translational Medicine; 2015; vol. 7, 290ra289.

Johansen, et al., FDA-approved Selective Estrogen Receptor Modulators Inhibit Ebola Virus Infection; Science Translational Medicine; 2013; vol. 5, 190ra179.

Johnson, et al., Pyridinyl imidazole inhibitors of p38 MAP kinase impair viral entry and reduce cytokine induction by Zaire ebolavirus in human dendritic cells; Antiviral Research; 2014; vol. 107, pp. 102-109.

Kamentsky, et al., Improved structure, function and compatibility for CellProfiler: modular high-throughput image analysis software; Bioinformatics; 2011; vol. 27, No. 8, pp. 1179-1180.

Koivusalo, et al., Amiloride inhibits macropinocytosis by lowering submembranous pH and preventing Rac1 and Cdc42 signaling; The Journal of Cell Biology; 2010; vol. 188, pp. 547-563.

Kouznetsova, et al., Identification of 53 compounds that Block Ebola virus-like particle entry via a repurposing screen of approved drugs; Emerging Microbes and Infections; 2014; vol. 3.

Kuhn, et al., Virus nomenclature below the species level: a standardized nomenclature for filovirus strains and variants rescued from cDNA; Archives of Virology; 2014; vol. 159, pp. 1229-1237.

Lopez-Castejon, et al., Understanding the mechanism of IL-1beta secretion; Cytokine & Growth Factor Reviews; 2011; vol. 22, pp. 189-195.

Lyles, et al., Vesicular Stomatitis Virus M Protein in the Nuclei of Infected Cells; Journal of Virology; Nov. 1988; vol. 62, pp. 4387-4392.

Macarron, et al., Impact of high-throughput screening in biomedical research; www.nature.com/reviews/drugdisc; Macmillan Publishers Limited; Mar. 2011; vol. 10, pp. 188-195.

Malecka, et al., Identification and Characterization of Small Molecule Human Papillomavirus E6 Inhibitors; ACS Chemical Biology; vol. 9; 2014; pp. 1603-1612.

Malyukova, et al, Macropinocytosis in Shiga toxin 1 uptake by human intestinal epithelial cells and transcellular transcytosis, American Journal of Physiology, Gastrointestinal and Liver Physiology; 2009; vol. 296, G78-92.

Marzi, et al., Ebola Vaccine. VSV-EB OV rapidly protects macaques against infection with the 2014/15 Ebola virus outbreak strain; Science; 2015; vol. 349, pp. 739-742.

Miller, et al., Inhibition of Ebola Virus Entry by a C-peptide Targeted to Endosomes; The Journal of Biological Chemistry; 2011; vol. 286, pp. 15854-15861.

Miller, et al., Ebolavirus Requires Acid Sphingomyelinase Activity and Plasma Membrane Sphingomyelin for Infection; Journal of Virology; 2012; vol. 86, pp. 7473-7483.

Misasi, et al., Filoviruses Require Endosomal Cysteine Proteases for Entry but Exhibit Distinct Protease Preferences; Journal of Virology; 2012; vol. 86, pp. 3284-3292.

Mudhasani,et al., High Content Image-Based Screening of a Protease Inhibitor Library Reveals Compounds Broadly Active against Rift Valley Fever Virus and Other Highly Pathogenic RNA Viruses; 2014; PLoS Neglected Tropical Diseases; vol. 8, e3095.

Nair, et al., Isolation and Generation of Human Dendritic Cells; Current Protocols in Immunology; 2012; Chapter 7, Unit 7.32.

Nanbo, et al., Ebolavirus is Internalized into Host Cells via Macropinocytosis in a Viral Glycoprotein-Dependent Manner. PLoS Pathogens; 2010;vol. 6, e1001121.

Qiu, et al., Reversion of advanced Ebola virus disease in nonhuman primates with ZMapp™; Nature; Oct. 2, 2014; vol. 514, pp. 47-53.

Rougeron, et al., Ebola and Marburg Haemorrhagic Fever; Journal of Clinical Virology, The Official Publication of the Pan American Society for Clinical Virology; 2015; vol. 64, pp. 111-119.

Saeed, et al., Cellular Entry of Ebola Virus Involves Uptake by a Macropinocytosis-Like Mechanism and Subsequent Trafficking through Early and Late Endosomes; PLoS Pathogens; 2010; vol. 6, e1001110.

Sakurai, et al., Two pore channels control Ebolavirus host cell entry and are drug targets for disease treatment; Science; Feb. 27, 2015; vol. 347, pp. 995-998.

Salata, et al., Amiodarone and metabolite MDEA inhibit Ebola virus infection by interfering with the viral entry process; FEMS Pathogens and Disease; 2015; vol. 73.

Schornberg, et al., Role of Endosomal Cathepsins in Entry Mediated by the Ebola Virus Glycoprotein; Journal of Virology; 2006; vol. 80, pp. 4174-4178.

Scott, et al., Ion flux and the function of endosomes and lysosomes: pH is just the start: The flux of ions across endosomal membranes influences endosome function not only through regulation of the luminal pH; BioEssays: News and Reviews in Molecu.

Simmons, et al., Ebolavirus Glycoprotein Directs Fusion through NPC1+ Endolysosomes; Journal of Virology;2015; vol. 90, pp. 605-610.

Thi, et al., Lipid nanoparticle siRNA treatment of Ebola-virus-Makona infected nonhuman primates; Nature; May 21, 2015; vol. 521, pp. 362-365.

\* cited by examiner

Complete curve,
high efficacy

Complete curve,
partial efficacy

Complete curve,
high efficacy,
poor fit

Complete curve,
partial efficacy,
poor fit

Curve does not reach zero
but compound effective

Complete curve,
high efficacy, does
not reach zero

No curve, complete
inhibition

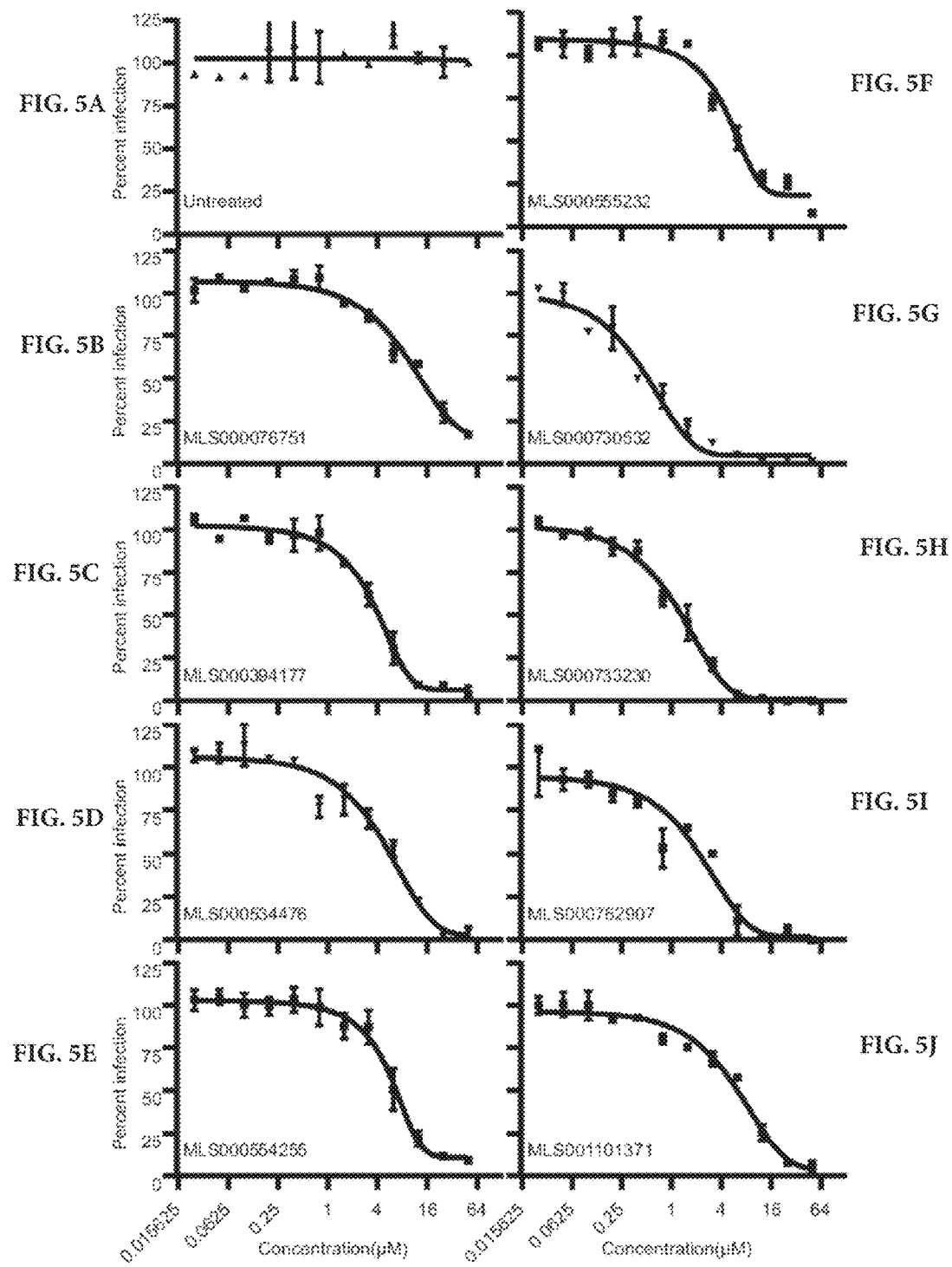

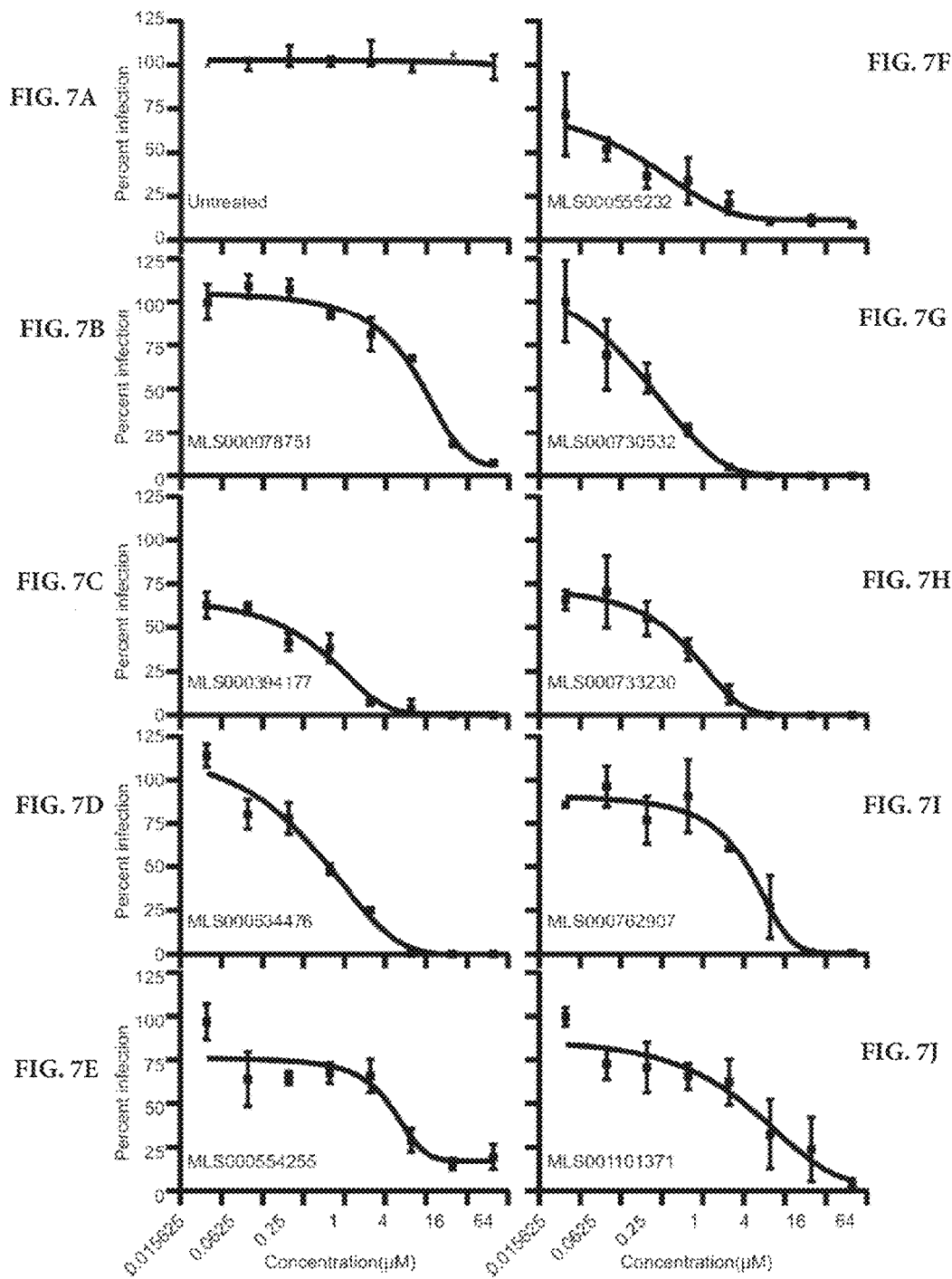

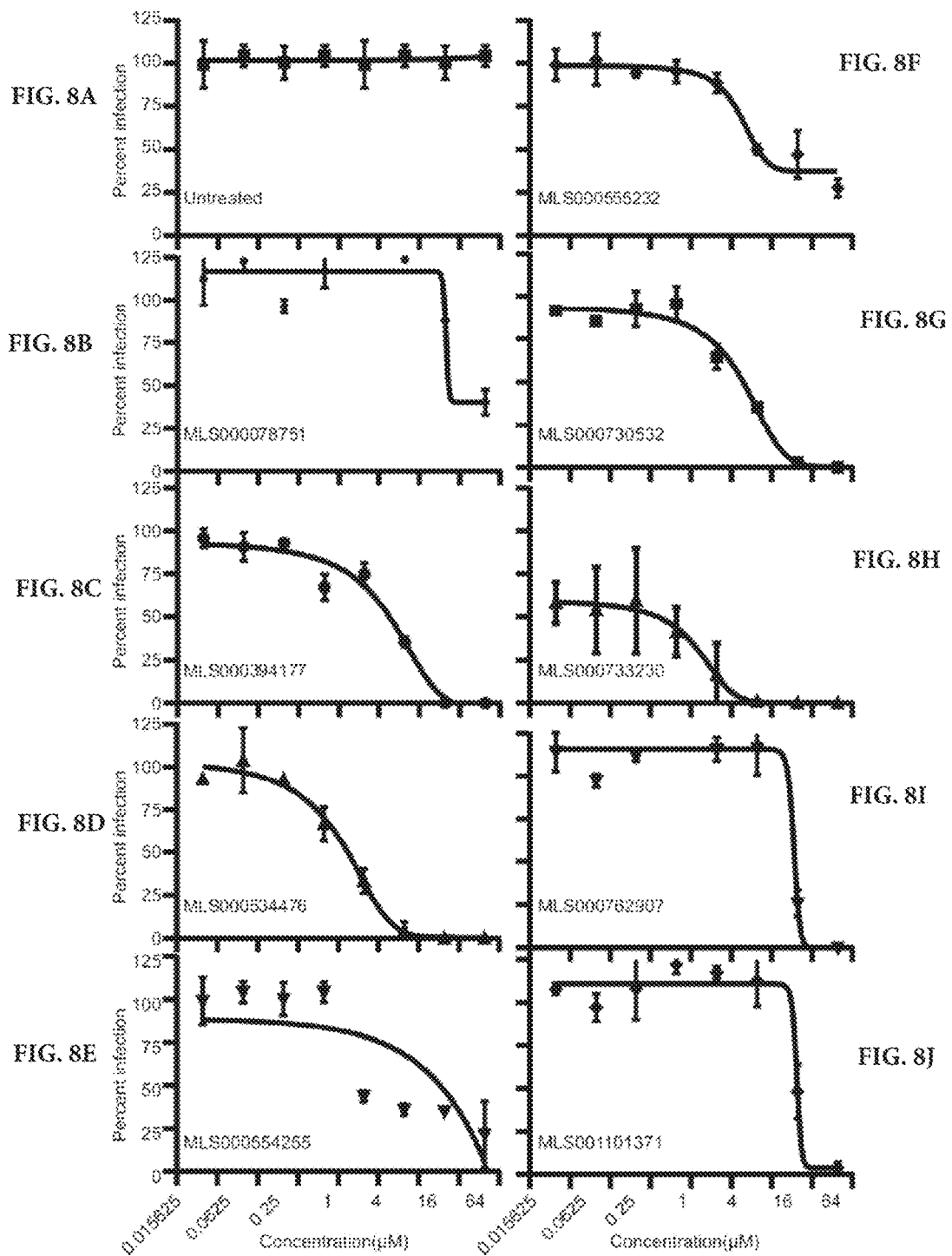

INHIBITORS OF MACROPINOCYTOSIS IN PREVENTION AND TREATMENT OF DISEASE

CROSS REFERENCE TO RELATED APPLICATION

This application claims priority to and the benefit of U.S. Provisional Application Ser. No. 62/318,092 filed Apr. 4, 2016, titled "Inhibitors of Macropinocytosis in Prevention and Treatment of Disease," the full disclosure of which is hereby incorporated herein by reference in its entirety for all purposes.

GOVERNMENT SUPPORT

This invention was made with government support under Grant Nos. R21 5R21AI115082-02, RO3 5R03MH086850-02, and RO1 AI077519 awarded by the National Institutes of Health and Grant No. HDTRA1-12-1-0002 awarded by the Department of Defense. The government has certain rights in the invention.

TECHNICAL FIELD

The present disclosure relates to certain inhibitors of macropinocytosis, and more specifically to compounds and methods for inhibiting macropinocytosis to block infection by certain viruses.

BACKGROUND

Macropinocytosis is an actin-dependent process initiated from surface membrane ruffles. In macropinocytosis, large endocytic vacuoles called macropinosomes mediate the non-selective uptake of macromolecules such as solute molecules, nutrients, and antigens. All animal cells take up extracellular fluid and substances through macropinocytosis which represents a portal of cell entry exploited by a range of pathogens.

The Filoviridae family includes highly infectious and pathogenic Ebolaviruses and Marburgviruses, and a recently identified member Lloviu. Since the first reported outbreak in 1976, each successive decade has seen an increase in recurrence of Filovirus outbreaks, incidences as well as number of infected people. Filoviridae are non-segmented, negative sense single stranded RNA viruses. Both Ebolaviruses and Marburgviruses are highly contagious and based on known outbreaks, average case fatality rates range from 42%-90%. According to WHO, the recent Ebola virus outbreak has resulted in more than 28,000 infections and more than 11,000 deaths.

Filovirus entry into cells is dependent on the single viral glycoprotein (GP). Though GPs of Ebolaviruses and Marburgviruses are quite distinct from each other, their entry mechanisms share common traits, offering potential broad-spectrum anti-Filoviral targets. Filoviral GP binds receptors; virus is internalized through macropinocytosis and trafficked through endosomes, which is dependent on the calcium channel, TPC2. During trafficking the virus is exposed to an increasingly acidic environment in which proteases are activated and cleave the GP, allowing interaction with NPC1, a key protein found in endosomes.

Several therapeutic candidates are currently undergoing clinical trials. Many of these drugs and therapies target only the current outbreak strain of Ebolavirus (previously named Zaire Ebolavirus) and closely related strains. However, there is still a need to be able to treat disease caused by other species of Ebola and Marburg viruses. Though Ebolaviruses and Marburgviruses are quite distinct from each other, they still share common traits that when inhibited by a small molecule may be useful as a broad-spectrum anti-filoviral agent.

Developing small molecules into drugs is inefficient with only 1 in 100,000 hits from a screen making it to the clinic. Large screens increase chances of eventually identifying active and specific small molecules that can be used as drugs. However, this work is hampered by the dangerous nature of Filoviruses, requiring high containment laboratories for all work. Instead, much of the recent progress in identifying anti-Filoviral compounds has been made by testing small libraries of clinically approved medications for other indications or other virus types. Identifying and developing specific and potent anti-Filoviral agents continues to be very challenging.

SUMMARY

Disclosed herein are compounds and methods addressing the shortcomings of the art, and may provide any number of additional or alternative advantages. Described herein are compounds, compositions and methods for inhibiting macropinocytosis, thus preventing infection by certain pathogens. Embodiments described herein include a pharmaceutical composition capable of inhibiting vesicle formation and having the general formula (I) or a pharmaceutically acceptable derivative thereof:

General formula (I)

The pharmaceutical composition can further include therapeutically effective amounts of a pharmaceutical composition having the general formula (I), and a pharmaceutically acceptable carrier. Certain embodiments include a method for treating or preventing a viral infection in a subject. The method includes administering to the subject therapeutically effective amounts of a pharmaceutical composition having the general formula (I). The viral infection can be a virus infection caused by a Filovirus. The viral infection can be an Ebolavirus infection. The viral infection can be a Marburgvirus infection. The viral infection can be caused by other viruses such as Respiratory syncytial virus, nipah virus, vaccinia virus, African Swine fever virus. Certain embodiments include a method for treating or preventing a bacterial or protozoan disease is a subject. The method includes administering to the subject therapeutically effective amount of a pharmaceutical composition having the general formula (I). The protozoan disease can be caused by protozoans such as *Trypanosome cruzii* or the different *Leishmania* species that have an intracellular life stage inside the mammalian host cell. The bacterial disease is any bacterium that has a stage of its life-cycle within the mammalian cell. Such bacteria include but are not limited to *Lysteria, Legionella, Salmonella, Francisella*, or *Mycobacteria*.

Embodiments described herein include a pharmaceutical composition capable of inhibiting vesicle formation and having the general formula (II) or a pharmaceutically acceptable derivative thereof:

General formula (II)

The pharmaceutical composition can further include therapeutically effective amount of a pharmaceutical composition having the general formula (II), and a pharmaceutically acceptable carrier. Certain embodiments include a method for treating or preventing a viral infection is a subject. The method includes administering to the subject therapeutically effective amount of a pharmaceutical composition having the general formula (II). The viral infection can be a virus infection caused by Filovirus. The viral infection can be an Ebolavirus infection. The viral infection can be a Marburgvirus infection. Certain embodiments include a method for treating or preventing a bacterial or protozoan disease is a subject. The method includes administering to the subject therapeutically effective amount of a pharmaceutical composition having the general formula (II). The protozoan disease can be caused by protozoans such as *Trypanosome cruzii* or the different *Leishmania* species that have an intracellular life stage inside the mammalian host cell. The bacterial disease is any bacterium that has a stage of its life-cycle within the mammalian cell. Such bacteria include but are not limited to *Lysteria, Legionella, Salmonella, Francisella*, or *Mycobacteria*.

Numerous other aspects, features and benefits of the present disclosure may be made apparent from the following detailed description taken together with the drawing figures. The pharmaceutical compositions can include compounds described herein, other components, or ingredients depending on desired prevention and treatment goals. It should be further understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure can be better understood by referring to the following figures. The components in the figures are not necessarily to scale. The emphasis is instead placed upon illustrating the principles of the disclosure. In the figures, reference numerals designate corresponding parts throughout the different views.

FIG. 1A is a diagrammatic representation of the pseudotype production process for preparing Vesicular Stomatitis Virus (VSV) pseudotyped with Marburgvirus glycoprotein (GP). FIG. 1B is a diagrammatic representation of the pseudotype production process for preparing Murine Leukemia Virus (MLV) pseudotyped with Marburgvirus GP.

FIG. 2A is a representation of the signal to background of assay. FIG. 2B is a representation of the Z' trend across entire qHTS.

FIGS. 5A, 5B, 5C, 5D, 5E, 5F, 5G, 5H, 5I, and 5J are graphical representations of the dose dependent activity of compounds against MARV in HeLa cells.

FIGS. 7A, 7B, 7C, 7D, 7E, 7F, 7G, 7H, 7I, and 7J are graphical representations of the dose dependent activity of compounds against EBOV in HeLa cells.

FIGS. 8A, 8B, 8C, 8D, 8E, 8F, 8G, 8H, 8I, and 8J are graphical representations of the dose dependent activity of compounds against EBOV in primary human macrophages.

FIG. 11A is a series of images of HeLa cells pre-treated with 50 μM of indicated compounds for 1 h, followed by incubation with fluorescently labeled dextran (M.W.10,000, green). Cell nuclei (intense blue) and cytoplasm (weak blue) were stained with Cell Mask Blue. Lack of green staining indicates inhibition of macropinocytosis. FIG. 11B is a graphical representation of the average number of vesicles per cell. FIG. 11C is a series of images of HeLa cells serum starved for 4 h followed by treatment with compounds for 1 h in serum free medium. Treated cells were incubated with 25 μg/ml of transferrin conjugated to Alexa 488 for 20 min, unbound transferrin was washed off and cells fixed in formalin. Fixed cells were imaged. FIG. 11D is a graphical representation of the fluorescence intensity of transferrin taken into cells after excitation at 488 nm. Compounds that do not affect transferrin uptake but inhibit dextran uptake are specific inhibitors of macropinocytosis. FIG. 11E is a series of images of HeLa cells incubated with EBOV for 2.5 h in the presence of each indicated compound and then non-permeabilized cells stained for EBOV GP followed by an Alexa 546-labeled secondary antibody (red). Cells were then permeabilized and the staining repeated but using an Alexa 488-labeled secondary antibody. Cell bodies (blue) were stained with Cell Mask Blue. FIG. 11F is a graphical representation of the deconvolved image stacks used to generate 3D models of cells with bound virus particles using Imaris software. Internalized virus particles (green, not red) and cell numbers were counted. This test measures ability of compounds to inhibit overall virus uptake into cells by vesicular transport of which macropinocytosis is one type.

FIG. 12A is a graphical representation of the portion of VLPs colocalized with the early endosome vesicle marker, EEA1, shown as the average +/− st. dev. of more than 200 cells. Lower levels of EEA1 association indicate a block in vesicle-containing virus movement from the cell surface into the cell. FIG. 12B is a graphical representation of the portion of VLPs colocalized with the late endosome vesicle marker, LAMP1, shown as the average +/− st. dev. of more than 200 cells. Lower levels of LAMP1 association indicate a block in vesicle-containing virus movement from the early endosome to the late endosome which is needed for infection to take place.

DETAILED DESCRIPTION

Figure 1A:
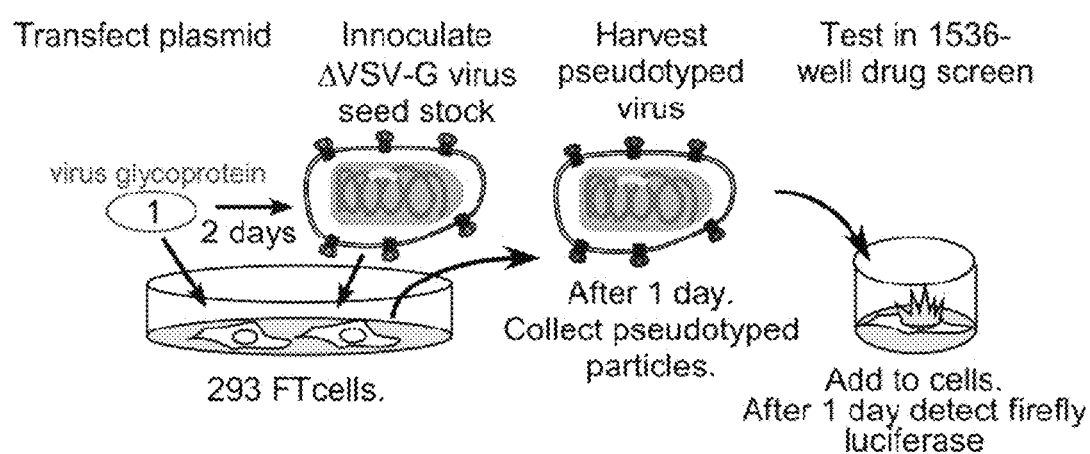
FIGS. 1A and 1B are diagrammatic representations of the pseudotype production process.

Reference will now be made to the exemplary embodiments illustrated in the drawings, and specific language will be used here to describe the same. It will nevertheless be understood that no limitation of the scope of the disclosure is thereby intended. Alterations and further modifications of the inventive features illustrated here, and additional applications of the principles of the inventions as illustrated here, which would occur to one skilled in the relevant art and having possession of this disclosure, are to be considered within the scope of the disclosure.

Filoviruses are highly infectious, with no available FDA-approved drug therapy. Most work to find a treatment has involved only a few strains from this diverse family of viruses and testing relatively small drug libraries or compounds that have shown efficacy on other virus types. High-throughput screening of 319,855 small molecules were conducted from the MLSMR library against Marburgvirus and a distantly related Ebolavirus. Of 17 novel small molecule inhibitors that blocked infection by both viruses, 9 were selected for detailed analysis including specificity, potency, and mechanisms of action. The compounds interfered with cell surface attachment, macropinocytosis-mediated uptake and endosomal trafficking. Two novel specific macropinocytosis inhibitors outperform EIPA, a commonly accepted macropinocytosis inhibitor, in both potency and lack of toxicity. These inhibitors not only have potential to be developed as anti-Filovirals but also offer treatment for other diseases that depend on macropinocytosis.

EBOV and MARV have high case fatality rates averaging above 40%. Successful palliative treatment of patients from the latest EBOV outbreak demonstrated the importance of early medical intervention. At the same time it emphasized the lack of availability of specific antiviral therapies, and prompted more thorough testing of promising vaccine and therapy candidates. However, most of these efforts targeted only one virus species. Like any RNA virus, Filoviruses can easily mutate and so development of drug resistance to any one antiviral compound is inevitable. Therefore, a robust therapy will require a cocktail of inhibitors targeting different steps of the viral replication cycle. To date, there has been no reports on a large scale screen for anti-Filoviral compounds.

Although significant progress in performing high throughput screening (HTS) at BSL4 has been made, it is still cumbersome and throughput is lower than needed to complete a large screen in a reasonable time. Certain embodiments of the disclosure include virus pseudotypes of MARV and EBOV to allow identification of inhibitors of virus entry into cells. The replication defective pseudotyped viruses allowed testing at lower biological containment and enabled the use of a state of the art robotics platform to assess efficacy of multiple concentrations of each compound during primary screening, (qHTS). This approach helps to eliminate false positive and negative hits by examining the dose-response curves of each compound. As qHTS increased the number of assay points required by 6-fold, high plating density, (1536-well format), was needed. This was a significant challenge to implement with a cell-based assay because as few as 1000 cells were present in each well and required high virus titers for the inoculum. Unfortunately, EBOV GP pseudotypes of sufficient activity could not be obtained due to toxicity of the GP in cells used to make the pseudotype. In contrast, MARV GP was not as toxic and sufficient virus titer was achieved.

Certain embodiments of the disclosure include qHTS methods with the infection reporter, firefly luciferase. Firefly luciferase provided high signal to noise (>100) and broad signal linearity (6 orders of magnitude) that can be sensitively detected. However, while the use of the pseudotype and luciferase reporter aided primary screening, counter-screening was needed to distinguish compounds impacting virus GP function from those that interfered with VSV replication and luciferase activity. Indeed, of the 7200 compounds that were identified from the primary screen, only 554 were effective in the retrovirus pseudotype-based counterscreen. All of the 7200 compounds are reported in PubChem (IDs 540276 and 720532) and may be useful as inhibitors of VSV or similar rhabdoviruses. Importantly, the approach of using the two pseudotypes to screen and counterscreen the library was validated when wild type viruses were used to check compound inhibition. A significant enrichment was seen for active compounds with 10% of the 554 compounds being active at <50 μM with either wild type MARV or EBOV. This represents a 100-fold enrichment over that seen when screening a random library of compounds for antivirals.

Of the most potent 61 novel compounds that inhibited MARV infection, 42 were also inhibitors of EBOV. This suggests that even though MARV and EBOV are distantly related and the GPs of each share less than 35% identity, there are conserved features that can be targeted by small molecules. Conversely, the other 19 compounds that only affected MARV indicates specific differences in cell entry which may be exploited in studying infection mechanism unique for each virus. Indeed, this is supported by work showing that each virus has different dependencies on cellular proteases for activation of the GP for membrane fusion and is potentially the reason that none of the broadly-active compounds were found to be cathepsin protease inhibitors.

Quantitative high resolution microscopy-based image analysis approaches were developed to identify the site of inhibitor activity. This was achieved using Cell Profiler platform, a freely available software image analysis tool as well as 3D image reconstruction of images of labeled virus interacting with labeled cells and organelles. This approach used robust assays and was quantitated using automated computer-based image analysis to evaluate hundreds of cells and thousands of virus particle-cell interactions. The analysis allowed unbiased segregation of compounds into those impacting binding to cells (MLS000078751 and MLS000534476), early uptake (MLS000394177, MLS000730532, MLS000733230), early endocytic trafficking (MLS000555232) and late endosome trafficking (MLS000554255 and MLS001101371). The same approach can be applied to similar anti-viral screens in the future and will enable better understanding of compound action. MLS000762907 did not block any of these steps and is likely a general inhibitor of endocytosis that targets steps other than the known markers of Filovirus cell entry that were tested.

One of the common features of Filovirus entry into cells is macropinocytic uptake of the large filamentous virus particle (up to 2 μm in length). The long filamentous form of the virus means virus particles are sterically precluded from classical endocytic uptake routes such as clathrin and caveolae-mediated endocytosis. Instead, macropinocytosis appears to play a dominant role in productive infection. However, in general as an endocytic uptake route, it remains poorly defined. Few macropinocytosis-specific inhibitors are available to study the pathway and only a small number of cellular proteins have been identified that distinguish it from other endocytic uptake mechanisms. Amilorides such as EIPA, which inhibit an endosomal $Na^+/H^+$ pump, have been extremely valuable as well accepted inhibitors of macropinocytosis and were helpful in defining EBOV uptake mechanism. Aside from amilorides, few other specific inhibitors of macropinocytosis are available. The finding that MLS000394177 and MLS000733230 appear to specifically block EBOV and dextran but not transferrin uptake indicate that they are novel macropinocytosis inhibitors. Importantly, these compounds are more potent than EIPA in inhibiting Ebola virus. The $EC_{50}$ of MLS000394177 is 1.9 μM for Ebolavirus inhibition which is 25 times better than EIPA. For MLS000733230 the $EC_{50}$ is 6.7 μM which is 7 times better than EIPA. Both compounds are not toxic up to 100 μM whereas EIPA is toxic at 37 μM.

A second common feature of Filovirus cell entry is the requirement for low pH to promote cleavage of the GP during endocytic trafficking as well as eventual virus to cell membrane fusion mediated by the cleaved GP. The known proteases that mediate cleavage reside in endosomes and are activated by low pH. Therefore, inhibitors of vesicle proton pumps are a potential class of broad-spectrum antiviral therapies. However, attempts to use Bafilomycin A1 or chloroquine have not been successful due to toxicity or low potency, respectively. MLS000394177, MLS000733230, MLS000730532 and MLS000534476 each affected endosomal acidification but not as dramatically as Bafilomycin A. Interestingly, three of these compounds (MLS000394177, MLS000733230, MLS000730532) also inhibited macropinocytosis. The change in endosomal acidification is not unusual as many compounds that alter vesicle trafficking also affect endosome acidification and vice versa, as each is closely coupled. Indeed, EIPA, the inhibitor of macropinocytosis, also decreases endosomal acidification to a similar extent to that seen for the compounds identified here.

A third class of inhibitors blocked passage of virus particles from the macropinosome to the early and late endosomes. MLS000555232 appeared to block movement to early endosomes. Two other inhibitors impacted passage from the early endosome to the late endosome (MLS000554255 and MLS001101371). In the case of MLS000554255, particles accumulated in EEA1 positive vesicles (83% increase) and did not advance to later compartments. While each of these compounds inhibit trafficking of EBOV, that happens through macropinocytosis, they do not inhibit transferrin uptake suggesting that they target a specific component of endosomal trafficking specific for EBOV. Another compound, MLS000762907 did not affect any of the studied steps of viral entry as tested here. However, it blocked uptake of transferrin into cells suggesting a role for a factor that is trafficked through a pathway involved in transferrin uptake and is necessary for virus to escape from the endosome.

In screening the MLSMR small molecule library, nine novel broad-acting Filovirus entry inhibitors were identified and the steps of entry at which each acts was determined, as summarized in Table 1. Using already annotated data in PubChem, these compounds were found to have been screened in more than 400 other assays targeting cellular processes or specific protein-ligand interactions. The compounds, except MLS000554255, were reported as active on average in 1.5% of these assays. This low rate suggests that the compounds are acting specifically and may provide insight into their cellular targets.

TABLE 1

Assays were grouped on whether they were identified as hits in cell-based or in vitro only systems.

| Compound | Total reported assays | Unique cellular assays reporting compound as active (%) | Unique in vitro assays reporting compound as active (%) |
| --- | --- | --- | --- |
| MLS000555232 | 731 | 0.69% | 0.00% |
| MLS000762907 | 639 | 1.59% | 0.48% |
| MLS001101371 | 535 | 0.56% | 0.00% |
| MLS000394177 | 715 | 2.69% | 0.29% |
| MLS000733230 | 705 | 1.57% | 0.14% |
| MLS000730532 | 713 | 2.39% | 0.29% |
| MLS000078751 | 906 | 1.34% | 0.34% |
| MLS000534476 | 773 | 1.83% | 0.27% |
| MLS000554255 | 808 | 0.14% | 4.40% |

MLS000394177, the macropinocytosis inhibitor, was active in assays for inhibition of Janus kinase 2 (JNK2), Synuclein activity and Shiga toxins A and B. Shiga toxins are known to be taken into cells by macropinocytosis. A role for JNK signaling or Synuclein in macropinocytosis has not been reported. Our hypothesis is that by inhibiting JNK signaling or Synuclein, these compounds disrupt the cytoskeletal rearrangement function of the JNK signaling molecules and Synuclein and thereby inhibit macropinocytosis. MLS000394177, MLS000730532, MLS000733230 and MLS000078751 were found to inhibit secretion of IL-1-Beta, which is involved in exocytosis. Exocytosis is also important in initiating macropinocytosis by delivering lipids to the cell surface that form the macropinosome and inhibition of exocytosis inhibits EBOV infection. The remaining majority of assays involved inhibition of various ion channels. As discussed above, such channels are known to play roles in macropinocytosis, endocytosis and in EBOV infection, however none of the compounds were structurally related to previously reported channel inhibitors. The compound MLS001101371 was an exception in being identified in only two other assays despite being tested in 535 different assays. This low hit rate reflects a very high specificity for Ebola virus and few other cellular targets. This predicts low side effects if the compound were to be developed as a therapy. The two assays tested for antagonists of the DNA repair gene TDP1 and acetylcholine receptor M1. A role for a DNA repair inhibitor is unclear but known antagonists of GPCRs, including acetylcholine receptors was recently reported to inhibit EBOV and MARV infection during endocytosis. MLS001101371 shares no similarity to the reported GPCR inhibitors that prevent EBOV infection and so may also represent a novel GPCR antagonist.

As used here, the following terms may have the following definitions:

A "pharmaceutical composition" refers to a mixture of one or more of the compounds described herein, or a pharmaceutically acceptable derivative thereof, as an active ingredient, and at least one pharmaceutically acceptable carrier or excipient. The purpose of a pharmaceutical composition is to facilitate administration of a compound to a subject. An embodiment provides a pharmaceutical composition including a compound of one of the formulae described herein, or a pharmaceutically acceptable derivative thereof, and a pharmaceutically acceptable carrier or excipient. In some embodiments, the pharmaceutical composition includes two or more pharmaceutically acceptable carriers and/or excipients.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the active ingredient. For example, the term "a pharmaceutically acceptable derivative thereof" of compounds of general formula (I) and (II) includes all derivatives of the compounds of general formula (I) and (II) (such as salts, pro-drugs, metabolites, esters, ethers, hydrates, polymorphs, solvates, complexes, and adducts) which, upon administration to a subject, are capable of providing (directly or indirectly) the compounds of general formula (I) and (II).

As used herein, the term "pharmaceutically acceptable salt" refers to those salts which retain the biological effectiveness and properties of the parent compound. And unless otherwise indicated, a pharmaceutically acceptable salt includes salts of acidic or basic groups which may be present in the compounds of the formulae disclosed herein. This disclosure also relates to a process for the preparation of the above pharmaceutically acceptable salts, their derivatives, their analogs, their tautomeric forms, their stereoisomers, their polymorphs, and pharmaceutical compositions containing them.

Certain embodiments relate to pharmaceutically acceptable salts formed by the compounds of general formula (I) and (II), their derivatives, their analogs, their tautomeric forms, their stereoisomers, their polymorphs and pharmaceutically acceptable compositions containing them. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bi sulfite, sulfonate, benzenesulfonate, p-bromophenylsulfonate, chlorobenzenesulfonate, ethanesulfonate, 2-hydroxy ethanesulfonate, methanesulfonate, naphthalene-1-sulfonate, naphthalene-2-sulfonate, p-toluenesulfonate, xylenesulfonate, tartarate, and the like.

Embodiments of the disclosure include pharmaceutical compositions including compounds of general formula (I) and (II), or a pharmaceutically acceptable derivative thereof, and a pharmaceutically acceptable carrier or excipient. Pharmaceutically acceptable ingredients, such as excipients, diluents, fillers, binders, and carriers can be inert or actively contribute to the delivery and distribution of the compounds of general formula (I) and (II). The formulations used in embodiments herein include excipients, such as microcrystalline cellulose, lactose monohydrate, hydroxypropyl cellulose, croscarmellose sodium and magnesium stearate, preferably at least about 50 wt %, such as in the range from about 50% to about 95 wt %, including the range from about 50-90 wt %, and more preferably in the range from about 55-85 wt %, such as in the range from about 60% to about 85 wt %, or in the range from about 65 wt % to about 80 wt %, including about 60 wt %, about 65 wt %, about 70 wt %, about 75 wt %, or about 80 wt %.

Embodiments of the disclosure include the compound of general formula (I) with international union of pure and applied chemistry (IUPAC) name N-(2-morpholin-4-yl-ethyl)-3-nitro-4-(1-phenyltetrazol-5-yl)sulfanylbenzenesulfonamide. The structure of which is:

As an inhibitor of macropinocytosis, this compound is also known by the following synonyms: T5345352, SMR000248580, AC1NJ4BY, MLS000394177, MLS003914408, CHEMBL1372119, MolPort-005-316-290, HMS2562D03, ZINC25784472, and MCULE-5646150983.

Embodiments of the disclosure include the compound of general formula (II) with international union of pure and applied chemistry (IUPAC) name: 1-[[3-(2,5-dimethylthiophen-3-yl)-1-(2-fluorophenyl) pyrazol-4-yl] methyl]-4-pyridin-4-ylpiperazine. The structure of which is:

As an inhibitor of macropinocytosis, this compound is also known by the following synonyms, Ambcb47974179, MLS000733230, CHEMBL1304808, HMS2656I08, MCULE-3468920285, and SMR000318759.

Embodiments of the disclosure include use of these compounds as macropinocytosis inhibitor and drugs to treat infections and conditions that involve macropinocytosis. These compounds can also be used in research to study the process of macropinocytosis and dependent cell processes. These compounds can be used as drugs to prevent and treat infections with identified and as yet unidentified members of the Filovirus family, bacterial infection, protozoan infection, cancer, obesity, metabolic diseases, Leukemia, anti-itch and anti-chronic pain, cardiovascular, neurological, renal and metabolic disorders, short- and long-QT syndromes, Andersen syndrome, Cryopryrin-Associated Periodic Syndrome (CAPS), Chronic Obstructive Pulmonary Disease (COPD) and Schizophrenia.

As used herein, unless otherwise noted, the terms "treating", "treatment" and the like, shall include the management and care of a subject or patient (preferably mammal, more preferably human) for the purpose of combating a disease, condition, or disorder and includes the administration of a compound disclosed herein to prevent the onset of the symptoms or complications, alleviate the symptoms or complications, or eliminate the disease, condition, or disorder. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

In certain embodiments, the pharmaceutical compositions described above can also be used in combination with other known antiviral pharmaceuticals, such as Favipiravir, Brincidofovir, clomiphene, and toremifene. In certain other embodiments, the compounds can be administered in combination with convalescent plasma, zMapp, and other proposed therapeutics to offset infection. In certain embodiments, the pharmaceutical compositions described above can also be used in combination with other supportive therapy such as providing intravenous fluids (IV) and balancing electrolytes (body salts), maintaining oxygen status and blood pressure, and treating other infections. In certain embodiments, the pharmaceutical compositions described above can also be used in combination with antibody therapies targeting the virus glycoproteins or other virus components. Post exposure vaccination The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art. Compositions for administration herein may form solutions, suspensions, tablets, pills, capsules, sustained release formulations or powders.

An "effective amount" is an amount that will bring about the desired response in a subject, such as reduction in symptoms, prevention of infection, and elimination of existing viral infection in a subject. Illustratively, an effective amount of the compositions disclosed herein ranges from nanogram/kg to milligram/kg amounts for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician or veterinarian and methods for determining dose amounts and regimens and preparing dosage forms are described, for example, in Remington: The Science and Practice of Pharmacy, 22nd edition.

A large-scale screen of 319,855 small molecules from the MLSMR library was used as the starting point to identify inhibitors of GP mediated entry of Ebola virus (EBOV) and Marburgvirus Musoke (MARV). This study used the quantitative high throughput screening approach (qHTS) to rapidly identify true inhibitors. Results of the screen and mechanism of action for nine of the most potent broad-spectrum Filovirus inhibitors are presented. High throughput screening (HTS) strategies involves testing hundreds of thousands to millions of compounds for activity. Traditional HTS involves testing each compound at a single dose but is prone to false positive and negative outcomes requiring extensive follow up work to identify true hits and potentially missing active compounds respectively. qHTS seeks to overcome these problems, by testing compounds at multiple doses and quantitatively analyzing the dose response. Both HTS and qHTS provide the means to examine enough small molecules to obtain useful compounds that could be developed as treatments.

To date no HTS of a diverse small molecule library has been reported for any Filovirus. Here, qHTS of a 319,855 small molecule library was performed against Ebolavirus and Marburgvirus. Because initial screening had to be performed at low biological containment, pseudotypes were used. These pseudotypes are surrogates for wild type virus as they bear the glycoproteins of each virus that allow binding of receptors and entry into cells. This first step of the infection cycle is an attractive target for therapeutic intervention as blocking the virus would prevent establishment of infection and spread. Extensive counter-screening identified specific inhibitors of infection. Each of the candidate molecules were tested at BSL-4 with wild type Marburgvirus and Ebolavirus. Of the 319,855 compounds tested, 17 (0.005%) compounds (shown here as Table 2) inhibited both viruses and therefore are promising broad-spectrum antifilovirals. To understand their mechanism of action, quantitative modeling of virus for each step of the cell entry process was performed. Through this analysis 9 novel inhibitors were identified, two of which block macropinocytic uptake of virus, a poorly understood process used by a growing number of virus types.

TABLE 2

| Compound | Total reported assays | Unique cellular assays reporting compound as active (%) | Unique in vitro assays reporting compound as active (%) |
|---|---|---|---|
| MLS000555232 | 731 | 0.69% | 0.00% |
| MLS000762907 | 639 | 1.59% | 0.48% |
| MLS001101371 | 535 | 0.56% | 0.00% |
| MLS000394177 | 715 | 2.69% | 0.29% |
| MLS000733230 | 705 | 1.57% | 0.14% |
| MLS000730532 | 713 | 2.39% | 0.29% |
| MLS000078751 | 906 | 1.34% | 0.34% |
| MLS000534476 | 773 | 1.83% | 0.27% |
| MLS000554255 | 808 | 0.14% | 4.40% |

Figure 1B:
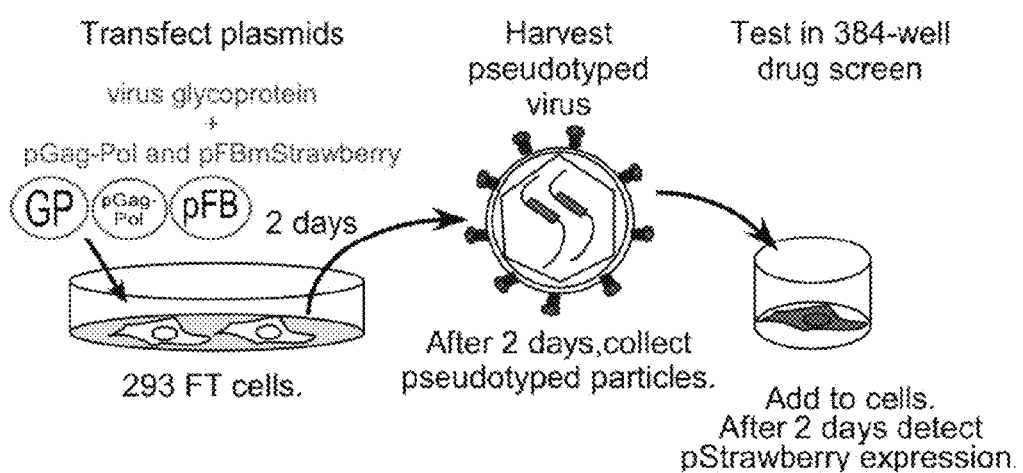

Filovirus entry into cells is dependent on the single glycoprotein (GP). GP binds receptors, mediates internalization through macropinocytosis and trafficking through endosomes. During trafficking the virus is exposed to an increasingly acidic environment in which proteases are activated to cleave the GP and allow interaction with NPC1, a key protein found in endosomes. Additional trafficking then occurs and involves the calcium channel TPC2. Since screening large libraries within BSL4 is difficult, virus pseudotypes were used for screens. Initially, a vesicular stomatitis virus (VSV) pseudotype was used (FIG. 1A). Counter-screens were performed with retrovirus pseudotypes (FIG. 1B). This approach was needed to eliminate compounds that impacted the replication of the VSV genome as well as the luciferase reporter.

Figure 2A:
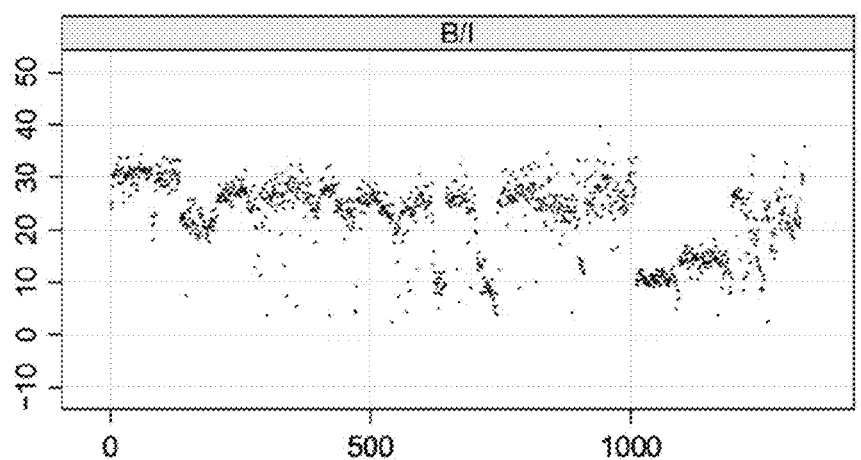
FIGS. 2A and 2B are representations of the qHTS screening performance.
Figure 2B:
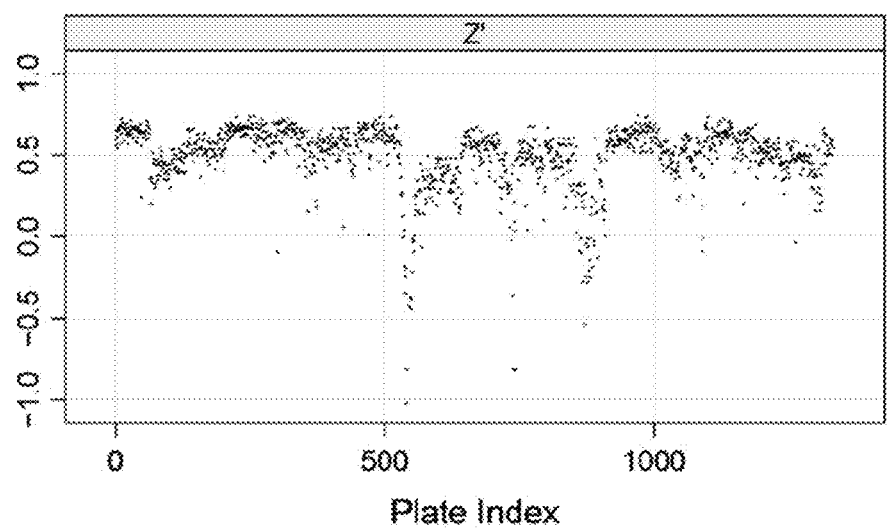
Figure 3A:
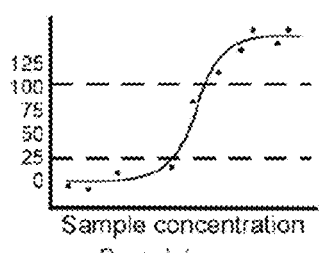
FIGS. 3A, 3B, 3C, 3D, 3E, 3F, and 3G are representations of the curve classification criteria for compounds.
Figure 3B:
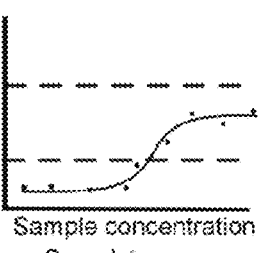
Figure 3C:
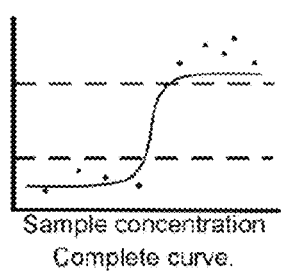
Figure 3D:
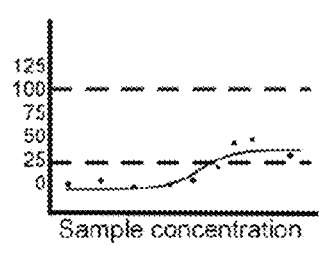
Figure 3E:
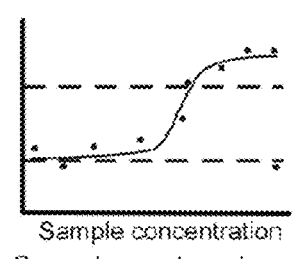
Figure 3F:
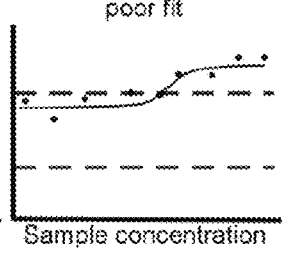
Figure 3G:
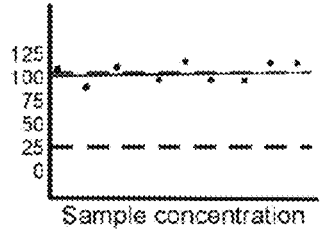

Certain embodiments of the disclosure include virus pseudotypes of Marburg virus and Ebola virus that were instrumental in the largest reported screen of small molecules to date against these two viruses. The replication defective pseudotyped viruses allowed identification of inhibitors of virus entry for each. The qHTS approach was used for the primary screen which takes advantage of testing multiple concentrations of each compound to prioritize the most potent and well behaved inhibitors (having complete dose response curves). However, as shown in FIG. 2A, qHTS suffered from requiring high plating density, (1536-well format) and was a challenge to optimize the assay to perform sufficiently. Only Marburgvirus pseudotypes gave Z' scores that were acceptable for screening (as shown in FIG. 2B). The qHTS approach helped to eliminate potential false negative and positive hits.

The assay used firefly luciferase as the reporter of infection. Luciferases are well suited for screening as they have high signal to noise (>100) and broad signal linearity that can be sensitively detected using photodetectors. Of the 7200 compounds that were identified from the primary screen, only 554 inhibited the retrovirus pseudotypes that were used as counterscreen. This filter worked to reject inhibitors of VSV core replication as well as firefly luciferase inhibitors. These compounds may be useful for identification of inhibitors of VSV and other rhabdoviruses and are available through Pubchem (Pubchem assay IDs 540276 and 720532). Importantly, the approach of using the two pseudotypes to screen and counterscreen the library was validated when wild type viruses were used to check compound inhibition. About 10% of the 554 compounds were confirmed as active against either wild type EBOV or MARV at 50 µM or less, which is a 100-fold enrichment over that was seen when screening a random library of compounds for antivirals in other studies.

About 61 novel compounds were identified that inhibited MARV infection. Of these, 42 were also inhibitors of EBOV. This suggests that even though MARV and EBOV are distantly related and the GPs of each share less than 35% identity, certain common features are shared by the GPs that can be the target of small molecules. The 19 compounds that only impacted MARV also indicate that MARV and EBOV differ in certain aspects of cell entry which may be exploited in studying the infection mechanism of each and targeted therapeutic agents. Indeed, this is supported by work showing that each virus has different dependencies on cathepsins for activation of the GP for membrane fusion.

Identifying inhibitory compounds was followed by studies to understand their mechanisms of action. Quantitative high resolution microscopy-based image analysis approaches were developed to identify the site of inhibitor activity. This was achieved through 3D image reconstruction of high magnification images of labeled virus interacting with cells and organelles. This approach rapidly segregated compounds into those impacting cell binding (MLS000078751 and MLS000534476), early uptake (MLS000394177, MLS000730532, MLS000733230), early endocytic trafficking (MLS000555232), and late endosome trafficking (MLS000554255 and MLS001101371).

One of the common features of Filovirus entry into cells is macropinocytic uptake of the large filamentous virus particle (up to 2 µm in length). This unusual size means a requirement for non-classical endocytic uptake mechanisms. Macropinocytosis appears to play the dominant role in productive infection. However, in general as an endocytic uptake route, it remains poorly defined. Few specific inhibitors and known cell proteins exist that can distinguish it from other endocytic uptake mechanisms, such as clathrin-coated pits and caveolae. Amiloride and its derivative EIPA, inhibitors of a $Na^+/H^+$ pump, have been extremely valuable to the field as the only well accepted inhibitors of macropinocytosis as well as inhibitor of Ebolavirus infection. Our work has identified 2 novel inhibitors of macropinocytosis. MLS000394177 and MLS000733230, that reduce uptake of fluorescently labelled dextran into cells, an accepted marker of micropinocytosis, do not interfere with transferrin uptake (endocytosed through clathrin-mediated endocytosis) and also block Ebolavirus infection at the site of virus uptake, but after cell surface binding. Further work to identify the cellular targets of each compound can identify additional new components involved in macropinocytosis as well as Filovirus entry inhibitors.

A second common feature of Filovirus cell entry is the requirement for low pH to promote cleavage of the GP during endocytic trafficking as well as eventual triggering of virus to cell membrane fusion mediated by the cleaved GP. The known proteases that mediate cleavage reside in endosomes and are activated by low pH. The low pH-triggering of virus to cell membrane fusion is common to all pH-dependent viruses. Therefore, inhibitors of vesicular proton pumps are a potential class of broad-spectrum antiviral therapies. However, attempts to use Bafilomycin A1 or chloroquine have not been successful due to toxicity or low potency respectively. MLS000394177, MLS000733230, MLS000730532 and MLS000534476 each affected endosomal acidification. Interestingly, three of these compounds also inhibited macropinocytosis. EIPA, the known inhibitor of macropinocytosis also blocks endosomal acidification, this suggests that the target of the first 3 compounds may also be a proton pump, like the Na+/H+ exchanger that is blocked by EIPA. However, the close connection between pH and trafficking regulation, cannot rule out other targets.

A third class of inhibitors blocked passage of virus particles from the macropinosome to the early and late endosomes. MLS000555232 appeared to block movement from macropinosomes to early endosomes. In general, the step of moving macropinocytosed cargoes into the endocytic system is poorly understood and a deeper study of this compound will provide insight into the process. Two other inhibitors impacted passage from the early endosome to the late endosome (MLS000554255 and MLS001101371). In case of MLS000554255 particles accumulate in EEA1 positive vesicles (83% increase) and seem to be stuck in these vesicles without further trafficking. Some of these compounds can affect known steps of the entry pathway involving GP protease cleavage and/or interaction with the endosomal protein NPC1. While interaction with the C-loop of NPC1 were unaffected by all compounds, MLS000534476 reduced GP cleavage by cellular proteases. Also, none of the compounds identified after counter screening resembled other known NPC1 interaction inhibitors. MLS000762907 did not affect any of the studied steps of viral entry as tested here. This compound did not affect virus binding to cell surface or macropinocytic uptake of dextran but blocked uptake of transferrin in cells.

The sites of action for 9 novel broadly-acting Filovirus entry inhibitors were identified. The performance of these compounds in other assays conducted through the MLSMR screening network was reviewed. Each compound has been tested in >500 assays targeting cell processes or specific protein-ligand interactions. Upon network analysis of cell-based assays, nine compounds were identified to be associated with other specific assays. MLS000394177, MLS000730532, MLS000733230 and MLS000078751 inhibit secretion of IL-1-Beta. Interestingly, the first 3 are those that inhibit micropinocytosis. Bringing cell membranes to the cell surface by exocytosis is essential for triggering macropinocytosis. It is also known that IL-1B secretion occurs through exocytosis. Therefore, it is possible that a block in exocytosis could equally impact IL-1B secretion and Ebolavirus infection. Indeed, exocytosis blocking drug was previously reported to inhibit Ebolavirus infection. MLS000555232, MLS000534476 and MLS000394177 were identified as inhibitors of MDM2/A and MDM4/1, both E3 ubiquitin ligases. Ubiquitin ligases have again been shown to be important for membrane recycling, endocytosis as well as exocytosis. The remaining assays showed inhibition of various ion channels. As discussed above, such channels are known to play roles in macropinocytosis, endocytosis and in Ebolavirus infection. The compound MLS001101371 was identified in only two other assays despite being present in the library from the beginning. This suggests that this compound is relatively specific for Filovirus entry.

Optimal dosages to be administered may be readily determined by those skilled in the art, and will vary with the particular compound used, the mode of administration, the strength of the preparation, the mode of administration, the number of consecutive administrations within a limited period of time (for example, up to 60 minutes) and the advancement of the disease condition. In addition, factors associated with the particular patient being treated, including patient age, weight, diet and time of administration, will result in the need to adjust dosages. The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The following non-limiting examples are provided in order to further illustrate the present invention.

Materials and Methods

Cells.

293FT cells (Thermo Cat#R700-07), Vero cells, HeLa cells and SW-13 cells were maintained in DMEM (Fisher scientific, Cat#MT10017CV) supplemented with 10% fetal bovine serum (Gemini Bio-Products, Cat#100106)-Complete medium. Primary human macrophages were differentiated from buffy coat fraction of human blood (from South Texas blood and tissue center) according to published protocols. Briefly, mononuclear lymphocytes were isolated using leucosep tubes (Fisher scientific, Cat#19177522) resuspended in IMDM (Fisher scientific, Cat#SH3022801) and plated in 96 well plates (50,000 cells per well). After adhering for 1 h, unattached cells were washed off using IMDM. Attached monocytes were allowed to differentiate into macrophages for 7 to 8 days in IMDM containing 2% heat inactivated human serum (Corning Inc., Cat#35-060-C1), 100 U/ml penicillin, 100 µg/ml streptomycin, 1× non-essential amino acids (Fisher scientific, Cat#TMS001C), 50 µM 2-mercaptoethanol (Fisher scientific, Cat#ICN19470583) and 800 u/ml human M-CSF (Biolegend, Cat#574806). Adherent, monocytes where washed and media replaced on days 2 and 6, while they were differentiating. All cells were kept at 37° C. in a humidified incubator with 5% CO2.

Wild Type Virus Production.

For virus naming, the current recommendations of ICTV52 were used. Zaire Ebolavirus (Mayinga strain)-EBOV with insertion of GFP between the NP and VP3553 that was a kind gift of Dr. Heinz Feldmann (NIH, Rocky Mountain Laboratory, Hamilton), EBOV and Marburgvirus (Musoke strain)-MARV were grown in Vero cells. All work was done in a BSL4 (P4) lab at Texas Biomedical Research Institute. Culture supernatants containing virus were concentrated by pelleting through a 20% sucrose cushion. Briefly, culture supernatants from infected Vero cells were collected and cell debris removed by centrifugation at 1800×g for 15 min. Clarified supernatant was overlaid on a 20% sucrose cushion and the virus pelleted by centrifugation at 141,118×g for 2 h at 4° C. Virus pellets were resuspended in PBS and stored in aliquots at −80° C. until used.

Production of MARVGP-VSVluc.

For preparing MARVGP-VSVluc, 293FT cells grown in 10 cm$^2$ tissue culture dishes were transfected with 10 μg of plasmid expressing MARV-GP using calcium phosphate method. Two days post transfection cells were inoculated with a VSV seed stock. This stock was derived from a recombinant VSV with a deletion of VSV-G and insertion of firefly luciferase encoding gene, this was a kind gift of Dr. Sean Whelan from Harvard Medical School. It had been pseudotyped to bear the GP of Venezuelan equine encephalitis virus. This was useful as it reached high titer and the GP degraded quickly and inoculation of cells. One day post infection, culture supernatants containing the MARV GP pseudotyped viruses were harvested and tested for infection by measuring expression of firefly luciferase in 293FT cells.

Production of Replication-Defective MLV Pseudotyped with MARV GP.

Replication defective MLV, capable of a single round of infection to express a red fluorescent protein (pStrawberry), pseudotyped with MARV GP was produced. Briefly, 293T cells grown in 10 cm2 tissue culture dishes were transfected with 5 μg each of plasmids encoding MLV GAG-Pol, pFB-strawberry and MARV (Musoke) GP (15 μg total) using calcium phosphate method. One day post transfection the cells were washed once with medium containing no FBS or antibiotics and then overlaid with fresh complete medium. Two days post transfection the supernatant from transfected cells were collected, filtered through a 0.45 micron filter (to filter cell debris) and stored at −80° C. for further use.

Production of MARV and EBOV VLPs.

VLPs containing either MARV GP or EBOV GP were produced in 293FT cells. Plasmid DNA constructs encoding EBOV matrix protein VP-40, VP-40 fused to GFP (VP40-GFP) and nucleoprotein (NP) were used for the VLP structural backbone. Plasmid DNA encoding EBOV GP or MARV GP were added to backbone plasmid mix to generate either EBOV or MARV GP specific VLPs. Briefly, 293FT cells grown in 10 cm2 tissue culture dishes were transfected with 3.5 μg of VP40-GFP, 1.5 μg VP-40, 5 μg NP and 1 μg GP encoding plasmids. Twenty four hours post transfection the cells were washed once with medium containing no FBS or antibiotics and then overlaid with fresh complete medium. Two days post transfection supernatants were collected and cell debris removed by centrifugation at 1800×g for 15 min. Clarified supernatant was overlaid on 20% sucrose cushions and the VLPs pelleted by centrifuging at 141,118×g for 2 hours. VLP pellets were resuspended in PBS and stored in small aliquots at −80° C. till further use.

Primary Screening Using MARVGP-VSVluc.

Two μL of 293FT cell suspension were dispensed at 1000 cells/well into solid white 1536-well plates (Grenier) using a Multidrop Combi (Thermo Scientific). Following an overnight incubation at 37° C. and 5% CO2, 23 nL compound was transferred into each well using a pin tool (Kalypsys). The plate was incubated for 1 h at 37° C. and 5% CO2, then 3 μL MARVGP-VSVluc at a 1:100 dilution was added. After 1 d of incubation at 37° C., 5% CO2, 2 μL of luciferase detection reagent (prepared from D-Luciferin, Potassium salt powder, Goldbio, Cat#LUCK-100) was added. Plates were incubated for 15 min at ambient temperature and then read using a ViewLux plate reader (Perkin Elmer) to detect luminescence. Assays were performed in sub-saturating amounts of virus (multiplicity of infection (MOI)<0.5), therefore luciferase signals reflect the amount (titer) of virus able to infect the cells in presence of the compound.

Data was normalized to the median of the positive control (Bafilomycin) and DMSO only wells. Four-parameter logistic dose response curves were fitted to the data using a custom grid based algorithm. The fitting procedure produced IC50 (concentration of half-maximal inhibition of virus infection) and efficacy (maximal response) values. Fitted curves were also assigned a curve class used to assess the dose response curve quality. Briefly, complete dose response curves with efficacy >80% and well-defined upper and lower asymptotes were classified as 1.1 curves and are considered the best quality. Class 2.1 and 2.2 were incomplete curves having only one asymptote, with efficacy of 80% or higher and lower than 80%, respectively. Class 3 curves showed activity at only the highest concentration or were poorly fit and are considered inconclusive. Class 4 curves were inactive, having a curve fit of insufficient efficacy or lacking a fit altogether.

Secondary Screen Using MLV Pseudotyped with MARVGP.

Inhibitors identified from primary screening were tested in a secondary screen at a single concentration of 50 μM for inhibition of MLV pseudotype infection. All treatments and screening was done as duplicates, each replicate in a different plate. Briefly, 2,500 SW-13 cells in 25 μl medium per well were incubated overnight in 384 well tissue culture plates. On the day of assay, test compounds were diluted to 200 μM concentration in complete medium. Twenty five μl of this mixture was added to the cells to achieve a concentration of 100 μM. Twenty five μl of medium was removed from the wells. After 1 h of incubating at 37° C., 25 μl of MLV pseudotype-containing culture supernatant was added to cells. This brought the final concentration of the compound to 50 μM upon addition of virus. All infections were done to achieve a MOI of about 0.075 to 0.15. Cells were incubated for 24 h. One day post infection cells were fixed by immersing the plates in formalin for 24 h at 4° C. Formalin from fixed plates was decanted and plates were washed twice with PBS. Nuclei were stained using Hoechst (Life technologies, Cat#H3570) at 1:50,000 dilution and plates were imaged on a Nikon Ti Eclipse automated microscope. Bafilomycin at final a concentration of 10 nM was used as a positive control drug. Nuclei (blue) and infected cells (red) were counted using CellProfiler software.

Testing of Compounds for Inhibition of Infection by Wild Type MARV and EBOV.

MARV and an infectious EBOV expressing GFP were used in counter screens. Inhibitors identified in secondary screen were tested at 8 concentrations for activity. All treatments and screening was done in duplicates for each virus, each replicate being in a different plate. New lots of compounds from different manufacturer were tested against wild type EBOV. Briefly, 4,000 HeLa cells per well in 25 µl of medium were grown overnight in 384-well tissue culture plates. On the day of assay, test compounds were diluted in 200 µM concentration in complete medium. 25 µl of this mixture was added to the cells already containing 25 µl medium to achieve a concentration of 100 µM. 25 µl of medium was removed from the first wells and added to next well. This type of serial dilution was done 8 times to achieve concentrations of 100, 50, 25, 12.50, 6.25, 3.12, 1.56 and 0.78 µM. These concentrations resulted in a final concentration of 50, 25, 12.50, 6.25, 3.12, 1.56, 0.78 and 0.39 µM upon addition of 25 µl of infection mix containing wild type virus. One hour after incubating with the drug, Bafilomycin at final a concentration of 10 nM was used as a positive control drug. Primary human macrophages were differentiated from monocytes in 96 well plates. Macrophages differentiated from plating of 50,000 monocytes per well resulted in approximately 3600 macrophages per well. These macrophages were treated with the same concentration of compounds as described above in 100 µl final volume per well. All wild type virus infections were done in a BSL-4 lab to achieve a MOI of about 0.075 to 0.15. Cells were incubated for 24 hours. One day post infection cells were fixed by immersing the plates in formalin overnight at 4° C. Fixed plates were decontaminated and brought out of the BSL-4. Formalin from fixed plates was decanted and plates were washed thrice with PBS. MARV infected plates and wild type EBOV infected plates were immunostained using virus specific antibodies, while plates with GFP encoding EBOV were stained for cell nuclei only. Nuclei were stained using Hoechst at 1:50,000 dilutions. Plates were imaged and nuclei and infected cells were counted using Cell Profiler software.

Immunostaining of MARV and EBOV Infected Plates.

Cells were permeabilized using 0.1% Triton X-100 (Sigma, Cat#T8787) in PBS and blocked for 1 h in 3.5% bovine serum albumin (Fisher-scientific-Cat#BP9704100). Fixed cells were incubated with an anti-MARV VLP antibody (IBT Bioservices, Cat#04-0005, 1:1500 dilution) or anti-EBOV GP antibody (IBT Bioservices, Cat#0201-020, 1:1500 dilution), overnight at 4° C. After 2 washes to remove any excess antibody cells were stained with anti-Rabbit Alexa-546 antibody (Life technologies, Cat#A11035). After 3 washes to remove any non-specific antibody nuclei were stained using Hoechst at 1:50,000 dilution and imaged on a Nikon Ti Eclipse automated microscope. Nuclei and infected cells were counted using CellProfiler software.

Effect of Compounds on Localization of EBOV Particles with Respect to Cells.

HeLa cells were grown in 8-well chamber slides (IBIDI, Cat#80826) at 20,000 cells per well. All treatments were done in duplicate for each virus, each replicate being on a different slide. Cells were treated with compounds of interest for 1 h at a concentration of 50 µM. One hour after incubation with compound, cell were challenged for 2.5 h with wild type EBOV. Infected cells were washed 3 times in PBS and fixed by immersing the slides in 4% paraformaldehyde for 24 h at 4° C. Paraformaldehyde from the fixed slides was decanted and slides washed 3 times with PBS. Cells were immunostained (as described previously) without permeabilization, with a GP-specific antibody. Anti-mouse Alexa 488 antibody (Life technologies, Cat#A11029) was used as secondary antibody. After this the cells were permeabilized using 0.1% Triton X-100 in PBS and blocked again for 1 h in 3.5% bovine serum albumin. Cells were then immunostained stained again using anti-GP antibody. Excess antibody was washed off and the cells were then stained with anti-Mouse Alexa-546 antibody (Life technologies, Cat#A11030). After 3 washes to remove any non-specific antibody cell bodies were stained using HCS Cell Mask blue (Life technologies, Cat#H32720) as per manufacturer's protocol. Cells were imaged across the z-plane on a Nikon Ti Eclipse automated microscope. Images were deconvolved using AutoQuant X3 software (Media cybernetics Inc.). Deconvolved images were analyzed using Imaris 3D image analysis software (Bitplane Inc.). For this 3D analysis, cell bodies were modelled on cell mask blue outline. Cell surfaces were modelled based on cell mask blue periphery. Virus particles which were red or green were modelled. Red particles within cell body were counted as particles inside. Green particles within 1 micron distance of cell surface were counted for surface interaction.

Effect of Compounds on Macropinocytic Uptake.

Cells were treated with compounds of interest for 1 h at a concentration of 50 µM in triplicates. After 1 h a mixture of 25 µg dextran, Alexa Fluor 488, 10,000 MW (Life technologies, Cat#D-22910) and Hoechst at a concentration of 1:10,000 was added to cells. After 30-40 minutes of incubation, images of live cells were captured (minimum 3 per well). Number of dextran vesicles in each image was counted using Cell Profiler.

Effect of Compound Treatment on Transferrin Binding and Uptake.

HeLa cells in 12 well plates were used for binding study while cells plated in a 96 well plate were used for uptake study. Cells were serum starved for 4 h followed by treatment with compounds at 50 µM for 1 h in serum free medium. Treated, serum starved cells in 12 well plates were then transferred to a 14° C. water bath and kept in it for 45 min. Cells were incubated with 25 µg/ml of human transferrin (Cat#T3309-Sigma-Aldrich) for 40 more min. Cells were washed twice with PBS at 14° C. to wash off unbound transferrin and lysed using cell extraction buffer PTR (300 µL). Amount of transferrin in lysates (bound to cells) was estimated using ELISA (Human Transferrin ELISA kit SimpleStep ab187391—Abcam).

For uptake studies, serum starved and compound treated cells were incubated with 25 µg/ml of transferrin conjugated to Alexa 488 for 20 min. Cells were washed twice with PBS at room temperature to wash off unbound transferrin and fixed in 10% neutral buffered formalin (VWR, Cat#16004-126). Fixed cells were imaged and intensity in 488 channel was measured using cell profiler. Intensity data was exported to FCS express (deNovo software). Non-transferrin treated cell intensities were used to determine baseline and cells corresponding to this intensity were excluded from analysis. Percent of transferrin positive cells for each treatment was plotted.

Colocalization of EBOV VLPs with Early Endosomal Marker EEA-1 and LAMP-1.

HeLa cells were grown in 8 well chamber slides (IBIDI—Cat#80826), 20,000 cells/well. All treatments were done in duplicates for each virus, each replicate being in a different slide. Cells were treated with compounds of interest for 1 h at a concentration of 50 µM. After 1 h of incubation with compound, cell were infected with fluorescent EBOV VLPs for 2 h 30 min at 37° C. in a humidified incubator with 5% CO2. After infection the cells were washed twice with PBS and fixed in 4% paraformaldehyde (Electron Microscopy Science, Cat#15710) overnight at 4° C. Fixed cells were washed thrice to remove paraformaldehyde, cells were permeabilized using 0.1% TritonX-100 (Sigma, Cat#T8787) in PBS and blocked for 1 h in 3.5% bovine serum albumin (Fisher-scientific—Cat#BP9704100). Fixed cells were incubated with an anti-EEA1 antibody (BD transduction laboratories, Cat#610457) at 1:2,000 dilution and anti-LAMP-1 antibody raised in rabbit (Cell signaling technology—Cat#9091) at 1:200 dilution for 2 h at 37° C. Excess antibody was washed off and the cells were then stained with anti-Mouse Alexa-647 antibody (Life technologies, Cat#A21236) and anti-rabbit Alexa-546 antibody and (Life technologies, Cat#A11035) at 1:1,000 dilution. After 3 washes to remove any non-specific antibody cell bodies were stained using HCS CellMask blue (Life technologies, Cat#H32720) as per manufacturer's protocol. Cells were imaged and sectioned across the z-plane on a Nikon Ti Eclipse automated microscope. Images were deconvolved using AutoQuant X3 software (Media cybernetics Inc.). Deconvolved images were analyzed using Imaris 3D image analysis software (Bitplane Inc.). EEA-1 positive vesicles, LAMP-1 positive vesicles and VLPs were modelled. VLPs colocalizing with EEA-1 and LAMP-1 were modelled and counted.

Acridine Orange Assay for Analysis of Compounds as Acidification Blockers.

Baby hamster kidney fibroblasts (BHK) cells were grown in minimal essential media (MEM) supplemented with 10% fetal bovine serum (FBS) at 37° C. and 5% CO2. Ten thousand (10,000) cells in 100 ml media were added to each well of a 96 well Falcon polystyrene, tissue culture plate and grown for 18-20 h, at which point the media was removed and replaced with 50 ml MEM+10% FBS+compound. Compounds were dissolved in DMSO and diluted in MEM+10% FBS; initial concentration was 100 µM. Bafilomycin A1 (100 nM) and 1% DMSO in MEM+10% FBS were used as positive and negative controls, respectively. After 4 h at 37° C., drug-containing media was removed and replaced with 100 ml of MEM+10% FBS+1 mg/ml acridine orange. Cells were incubated at 37° C. for 15 min and washed twice with 100 ml phosphate-buffered saline (PBS) for 5 min. Red and green fluorescence were measured with a Biotek Synergy 4 Multi-mode Microplate reader using 485/20 nm:665/7.5 nm and 485/20 nm:530/30 nm filter sets. All compounds were tested in triplicate. Data is presented as the mean±SEM ratio of red to green fluorescence. Statistical significance was determined by analysis of variance (ANOVA) with post-test comparisons to DMSO- and Bafilomycin-treated controls (GraphPad Prism).

EXAMPLES

The following Examples are set forth to aid in the understanding of the disclosure, and are not intended and should not be construed to limit in any way the invention set forth in the claims which follow thereafter.

Figure 4A:
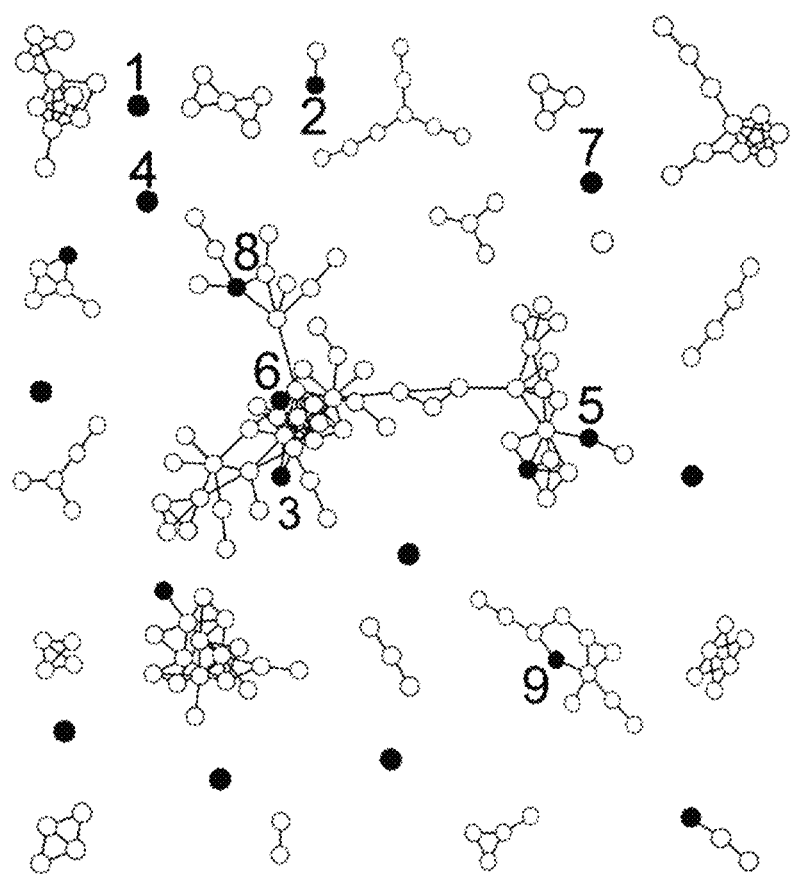
FIG. 4A is a representation of the compositional relationship of compounds from the screen confirmed active against wild type Ebola virus. Each circle represents one compound. Black circles indicate compounds that were evaluated in detail. Numbered black circles are compounds affecting vesicle transport and macropinocytosis.

Example 1—Optimization of a High Throughput Assay for Identifying Entry Inhibitors of MARV GP mediates the earliest steps of virus infection and is an attractive target for therapeutic intervention. By blocking virus entry, infection and spread can be treated before the virus has an opportunity to impact cell health. To specifically detect inhibitors of GP function, virus pseudotypes were used for primary screening. FIGS. 1A and 1B are diagrammatic representations of the pseudotype production process. FIG. 1A illustrates the process for preparation of Vesicular Stomatitis Virus (VSV) pseudotyped with MARV GP. The 293FT cells were transfected with a MARV GP expressing plasmid. At 2 days post transfection, cells were inoculated with a core VSV stock. This stock virus had a firefly luciferase encoding gene inserted in its genome and expressed Venezuelan Equine Encephalitis (VEE) Virus GP. The 1 day post infection culture supernatants containing pseudotyped viruses were harvested and tested for infection by measuring expression of firefly luciferase in infected 293FT cells. FIG. 1B illustrates the process for preparation of Murine Leukemia Virus (MLV) pseudotyped with MARV GP. The 293FT cells were transfected with plasmids expressing MARV GP, gag-pol and viral LTR sequences fused to red fluorescent protein pStrawberry. At 2 days post transfection, culture supernatants containing pseudotyped viruses were harvested and tested for infection by observing expression of pStrawberry in infected 293FT cells. Pseudotyped viruses bear the glycoproteins of one virus on the core of another virus type.

FIGS. 2A and 2B are a representation of the qHTS screening performance. Each plate corresponds to a 1536-well plate of compounds and controls. FIG. 2A shows the signal to background ratio of the assay. FIG. 2A shows the Z' trend across entire qHTS. Low Z' plates were rejected and rescreened during course of qHTS. VSV pseudotyped with MARV GP (MARVGP-VSVluc) and encoding firefly luciferase as a reporter with a titer of $10^{11}$ RLU/ml, corresponding to $10^9$ PFU/ml, were successfully produced. The MARVGP-VSVluc pseudotype yielded a signal to noise ratio of more than 30 (FIG. 2A) and a Z'-factor above 0.55 (FIG. 2B) in 1536-well format, indicating suitability for qHTS of the compound library. Extensive attempts to produce a pseudotype, using EBOV GP, with a similarly high titer were not successful.

Example 2—Identification of 7200 Compounds as Inhibitors of Infection by MARVGP-VSVluc Compounds in MLSMR library were screened at 6 concentrations each using an automated robotic assay platform at the National Center for Advancing Translational Sciences (NCATS). Compounds were prioritized based on curve class (FIGS. 3A, 3B, 3C, 3D, 3E, 3F, and 3G) and efficacy of reporter expression inhibition. FIGS. 3A, 3B, 3C, 3D, 3E, 3F, and 3G are a representations of the curve classification criteria for compounds. FIG. 3A is a representation of the complete curve; high efficacy:>80% activity; FIG. 3B is a representation of the complete curve; partial efficacy: <90%>80%; FIG. 3C is a representation of the complete curve; high efficacy; poor fit:>80%; FIG. 3D is a representation of the complete curve; partial efficacy; poor fit; FIG. 3E is a representation of the high efficacy incomplete curve as compounds were still found to be active at the lowest dose tested: minimum 25% activity. FIG. 3F is a representation of the High efficacy incomplete curve as compounds were still found to be active at the lowest dose tested: minimum 75% activity. FIG. 3G is a representation of the High efficacy no curve as compounds was found to be active at all tested concentrations: 100% activity. To eliminate compounds impacting luciferase reporter function, the hits were first filtered by removing compounds that showed activity in multiple unrelated assays performed at NCATS. Using this approach, 7200 compounds (2.3% of library) were identified as inhibitors of MARVGP-VSVluc infection (PubChem assay IDs 540276 and 720532).

Example 3—Counterscreening Using Retrovirus-Based Pseudotype

Counterscreening was performed to eliminate inhibitors of VSV genome replication and firefly luciferase, (used as reporter of infection), in the primary screen. A second pseudotype replacing the VSV core with that from Moloney murine leukemia virus (MLV) and the luciferase reporter with a red fluorescent protein, pStrawberry was used (FIGS. 1A and 1B). MLV shares little similarity with VSV in its replication strategy and luciferase and fluorescent proteins have different mechanisms for producing signals. Despite having 100-fold lower titer ($10^7$ focus forming units/ml) than the VSV pseudotype, the MLV pseudotype infection assay yielded a Z'>0.7 in 384-well plates. All 7200 compounds were tested at a single concentration of 50 μM to prioritize compounds of moderate or better potency. Cells were imaged by microscopy and the infection rate calculated. At the same time, those compounds reducing the total nuclei count by >20% were deprioritized as potentially impacting cell viability, cell cycle or adherence to the well. Of the 7200 hits, 554 compounds (7.7%) inhibited the MLV pseudotype infection by >90% without affecting the cell count. This observation suggested that >90% of the primary screen hits were either of low potency or impacted the VSV pseudotype and its luciferase reporter rather than MARV GP function. Chemical fingerprinting to determine structural relationship of the 554 compounds was done using Tanimoto criteria and is graphically represented in FIG. 4A. More than half of the compounds shared similarity with at least one other compound, forming 20 distinct groups of structurally related molecules. The remaining compounds appeared structurally unrelated to each other.

Example 4—Identification of 17 Novel Inhibitors of Both Wild Type MARV and EBOV Infection Compounds identified after counter-screening with the MLV pseudotype were tested for inhibition of wild type MARV and then EBOV. Each compound was tested at 8 doses ranging from 0.39 μM up to 50 μM in HeLa cells (a human cell line susceptible to infection by both viruses). Of the 554 compounds tested, 61 (11%) inhibited MARV infection by more than 80% at a minimum of one of the test concentrations and did not cause more than 20% reduction in cell number (TABLE 3).

TABLE 3

| Compound name | SMILES | Curve class (MARV) | IC-50 (MARV) | Curve Class (EBOV) | IC-50 (EBOV) |
|---|---|---|---|---|---|
| MLS000078751 | OC1=CC=C(C=C1)C(=C)C2=CC=C(O)C=C2 | 1.5 | 6.128 | 1.3 | 25.6 |
| MLS000394177 | C1=CC=C(C=C1)N2C(=NN=N2)SC3=CC=C(C=C3[N+](=O)[O-])S(=O)(=O)NCCN4CCOCC4 | 1.3 | 12.89 | 1.6 | 1.888 |
| MLS000534476 | NCCNC1=NC(C2=CC=CC=C2)=C3CCCCC3=C1C#N | 1.3 | 6.211 | 1.6 | 24.4 |
| MLS001239325 | Cl•CN(C)CCCN(C(=O)C1=C/C=C2/C=C\C=C/C\2=C\1)C3=N/C4=C/C5=C(OCO5)\C=C/4S\3 | 1.3 | 13.28 | 1.7 | 1.554 |
| MLS000555232 | COC1=CC2=C(C=C1)N=C3C=C(Cl)C=CC3=C2NC4=CC(CN5CCN(C)CC5)=C(O)C=C4 | 1.3 | 6.258 | 1.6 | 1.744 |
| MLS000730532 | CC=1C=C(N=C2C1C=C(C=C2)NC(=NCCCN3CCC4=CC=CC=C4C3)S)N5CCN(CC5)C | 1.3 | 1.929 | 1.1 | 1.557 |
| MLS000733230 | CC1=CC(=C(S1)C)C=2C(=CN(N2)C3=CC=CC=C3F)CN4CCN(CC4)C5=CC=NC=C5 | 1.3 | 11.67 | 1.3 | 6.698 |
| MLS000762907 | CC=1C(=C2N=C3C(=C(N2N1)NCCCN(C)C)CCCC3)C4=CC=CC=C4 | 1.3 | 12.54 | 1.3 | 3.188 |
| MLS001101371 | CC(C)N1CCN(CC1)C(=O)C2=C/C=C(OC3CCN(CCC4=C/C=C\C=C\4)CC3)\C=C\2 | 1.3 | 12.96 | 1.3 | 12.92 |
| MLS001030162 | CC1=C(C2=CC(=CC=C2N1CC3=CC=CC=C3)OC)CC[NH3+]•[Cl-] | 1.1 | 25.32 | 1.3 | 6.405 |
| MLS000666802 | CC(C)(C)C1=CC(=CC=C1OCCOCCNCC=C)Cl•C(=O)(C(=O)O)O | 1.1 | 25.17 | 1.5 | 0.6157 |
| MLS000999960 | Cl•CC1=C/C(NC(=O)CCN2CCN(C\C=C\C3=C\C=C/C=C\3)CC2)=C\C=C\1Br | 1.1 | 26.4 | 1.6 | 3.276 |
| MLS001173370 | Cl•FC1=C/C=C(\C=C\1)C(=O)CCCN2CC\C3=C(C2)\C4=C\C(F)=C/C=C\4N3 | 1.1 | 25.14 | 1.3 | 3.058 |
| MLS001174896 | O=C(C#CC1=C/C=C\C=C\1)C2=C/C=C/C=C\O\2 | 1.1 | 12.25 | 1.1 | 12.38 |

TABLE 3-continued

| Compound name | SMILES | Curve class (MARV) | IC-50 (MARV) | Curve Class (EBOV) | IC-50 (EBOV) |
|---|---|---|---|---|---|
| MLS001196083 | Cl•CC1═C/C(C1)═C\C(C)═C\1OCCN2\C═C/N═C\2 | 1.1 | 2.058 | 1.1 | 6.187 |
| MLS001239358 | Cl•CCOC(═O)N1CCN(CC1)S(═O)(═O)C2═CC═C(C═C2)C(═O)N(CCCN(C)C)C3═NC4═C(C)CC(C)═CC═C4S3 | 1.1 | 13.04 | 1.6 | 0.6092 |
| MLS001177927 | Cl•CC(NCC(O)COC1═C(C)/C═C\C═C\1C)C2═C/C═C\C═C\2 | 1.2 | 25.77 | 1.5 | 6.424 |
| MLS001209453 | COC1═C/C═C(NC2═C/C(C)═N\C3═C\C═C(OC)/C═C\2\3)\C═C\1 | 1.2 | 12.47 | 1.3 | 3.403 |
| MLS000580080 | CCOC1═CC═CC(═C1OCC2═CC═C(C═C2Cl)Cl)CNCCO•Cl | 1.2 | 25.05 | 1.3 | 24.6 |
| MLS000106706 | CC1═CC(OCCCCCNCCO)═CC(C)═C1Cl | 1.2 | 25.24 | 1.5 | 0.5953 |
| MLS001175455 | CCN(CC)CCNC(═O)C1═C/C═C(NC(═O)C2═C/C═C\C═C\2\C3═C\C═C(/C═C\3)C(F)(F)F)\C═C\1 | 1.2 | 25.45 | 1.6 | 6.419 |
| MLS000772389 | CCN(CC)CCCNC═1C═2C3═C(SC2N═C(N1)CN4CCOCC4)CCC3 | 1.2 | 24.76 | 1.6 | 3.508 |
| MLS000042810 | CC1CC(═C)CC(O1)C2═CC═CC═C2OCC(O)CN3CCCCC3 | 1.2 | 25.5 | 1.7 | ~-2.829 |
| MLS001162808 | COC1═C/C═C\C═C\1CCN2CCCC(CN(C)CC(C)(C)CO)C2 | 1.2 | 26.09 | 1.3 | 7.248 |
| MLS000684231 | CCOC(═O)C1═C(N(C═2C1═CC═C(C2)Br)OC)CC(CN(C)C)O)C•Cl | 1.2 | 4.878 | 1.3 | 6.477 |
| MLS000556387 | CCN(CC)CCNC1═NCCN2C1═CC3═C2C═CC(OC)═C3 | 1.2 | 25.46 | 1.6 | 2.929 |
| MLS001179278 | COC1═CC2═C(SC3═C(C═C(OC)C═C3)C(C2)N4CCN(C)CC4)C═C1 | 1.2 | 12.5 | 1.6 | 6.49 |
| MLS000567464 | CC1═CC(═C(S1)NC(═O)CCl)C(═O)C2═CC═CC═C2 | 1.2 | ~44.36 | 1.6 | 25.21 |
| MLS000583959 | CC1═CC═C(C═C1)N(C(C2═CC═C(C═C2)OC)C(═O)NC3CCCCC3)C(═O)CCl | 1.2 | 12.13 | 1.3 | 12.4 |
| MLS001018888 | CCN1CCCC1CNCC(COC2═CC═C(C═C2C)C(C)(C)C)O•C(═O)(C(═O)O)O | 1.2 | 25.65 | 1.3 | 12.23 |
| MLS001047402 | CN(C)C1═CC(═C2C═CC═CC2═N1)NC(═O)CN3CCCC3•C(═O)(C(═O)O)O | 1.2 | 25.93 | 1.2 | 5.259 |
| MLS001029946 | CC1═CC(═NC(═N1)N2CCOCC2)NC3═CC═C(C═C3)Cl | 1.2 | ~43.21 | 1.6 | 1.522 |
| MLS000332573 | CC1(CC(CC(N1)(C)C)NC(═O)N2C3═CC═CC═C3SC═4C2═CC═CC4)C | 1.2 | 12.76 | 1.3 | 6.022 |
| MLS000936259 | COC1═C/C═C═C(NC(═O)C2C3OC4(\C═C/3)C2C(═O)N(CCN5CCCCC5)C4C(═O)NC6CCCC(C)C6)\C═C\1 | 1.2 | 25.34 | 1.3 | 12.46 |
| MLS000718690 | CCOC1═CC(═CC(═C1OC)C1)CNCCC2═CNC═3C2═CC═CC3•Cl | 1.2 | 25.33 | 2.1 | 2.77 |
| MLS000880330 | FC1═CC═C(C═C1)C(N2CCN(CC2)C3CCCCC3)C4═NN═NN4CC5═CC═CS5 | 1.2 | 25.77 | 1.6 | 6.385 |
| MLS001207131 | CN(C)CCCN═C(S)N1CCN(CC1)C2═N/C(═C\S\2)/C3═C/C═C\C═C/3 | 1.2 | 25.29 | 1.3 | 25.21 |

TABLE 3-continued

| Compound name | SMILES | Curve class (MARV) | IC-50 (MARV) | Curve Class (EBOV) | IC-50 (EBOV) |
|---|---|---|---|---|---|
| MLS000673118 | CCCN1CCN(CC1)CCC NC(=O)C2=CC=3C(S2)= C4C=C(C=CC4=NC3 O)C | 1.2 | 25.11 | 1.3 | 25.01 |
| MLS000689481 | CCCCN(CCCC)CCNC (=O)CSCC1=CC=C(C=C 1)C•C(=O)(C(=O)O)O | 1.2 | 12.81 | 1.3 | 12.03 |
| MLS000554255 | CC(C)(CS([O-]) (=O)=O)NC(=O)CC[N+] (C)(C)CCO | 1.3 | 6.393 | 1.5 | 6.843 |
| MLS001179272 | FC1=CC2=C(C=C1)C (CC3=C(S2)C=CC(C1)= C3)N4CCN(CCC5OCC O5)CC4 | 1.3 | 25.41 | 1.5 | 0.6907 |
| MLS002702500 | COC1=C(OC)C=C(C=C 1)C2C(COC(C)=O)C(= C)C(=O)C3=C2C=CS3 | 1.3 | 2.061 | 1.1 | 5.931 |
| MLS001180408 | CN(C)CCCNC(=O)C(\N C(=O)C1=CC=C(C)C= C1)=C/C2=CC=C(O2)C 3=CC=C(C=C3)[N+]([O-])=O | 1.1 | 12.48 | 4 | |
| MLS000737975 | OC1=C/C=C(NC2=C/C= N\C3=C\C(Cl)=C/C=C\ 2\3)\C=C\1 | 1.1 | 25.23 | 4 | |
| MLS001237534 | CC1=C/C=C\C=C\1NC (=O)CSC2=C/C=C(\N=N\ 2)/C3=C/C=C\C=N/3 | 1.1 | 24.81 | 4 | |
| MLS000336293 | CC1=CC=C(C=C1)NC (=O)CN(C)C(=O)CN2C (=O)C(=C(C=N2)Cl)Cl | 1.1 | 24.03 | 4 | |
| MLS000780111 | C=1C=C2C(=CC1C(=O) CC1)NC(=O)CO2 | 1.1 | ~38.84 | 4 | |
| MLS001179997 | OC(=O)C(O)=O•CCN(C CNCC(O)COC1=C/C= C\C=C\1C(C)C)C2=C/C= C\C(C)=C\2 | 1.1 | 25.5 | 1.4 | |
| MLS000418057 | C1=CC=C(C=C1)CN2C CC(CC2)NC(=S)NC3= CC=C(C=C3)Cl | 1.2 | 25.6 | 4 | |
| MLS000936795 | CN(C)CCNC(=O)C1=C (C)/C2=C/C=C\C=C/2 O\1)S(=O)(=O)N3CCC C3 | 1.2 | 25.38 | 1.4 | |
| MLS000092187 | ClC1=CC=C(C=C1)N2 C(N3CCCC3C2=O)C4= CC=CS4 | 1.2 | 25.19 | 1.4 | |
| MLS000391391 | C1=CC=C(C=C1)C2=C SC(=N2)NC(=O)COC(= O)/C=C/C3=CC=CS3 | 1.2 | 25.29 | 1.4 | |
| MLS000569139 | CC1=CC=C(C=C1)NC (=O)ON=C2CCCC2 | 1.2 | 12.7 | 1.4 | |
| MLS001045935 | COC1=CC=CC=C1C(= O)ONC(=N)C2=CC=C C=N2 | 1.2 | 27.89 | 1.4 | |
| MLS001181479 | OC(CN1C2=C/C=C(Cl)\ C=C\2\C3=C\C(C1)=C/ C=C1\3)CN4CCCCC4 | 1.2 | 25.62 | 4 | |
| MLS000391984 | CC(C)(C)C1=CC(=CC (=C1O)C(C)(C)C)C=NO | 1.2 | 6.121 | 1.4 | |
| MLS000063146 | O=C(NC1CCCCC1)C2= CC=C(C=C2)S(=O)(= O)N3CCCCC3 | 1.2 | 25.39 | 4 | |
| MLS000768081 | CC1=CC=C2C(=C1)C (=CC(=N2)C)NC3=CC= C(C=C3)C(=O)NCCO)C | 1.2 | 13.83 | 4 | |
| MLS000091920 | CCN1CCN(CCCNC(=O) C2=CC3=CC4=CC=C (OC)C=C4N=C3O2)CC1 | 1.2 | 5.397 | 4 | |
| MLS001150589 | COC1=CC=C(C=C1)C (CNC(=O)C2=C(C)C3= CC(OC)=CC=C3O2)N4 CCCC4 | 1.2 | 25.87 | 4 | |
| MLS000736237 | C=1C=C(C=CC1CN2C CN(CC2)C3=CC=C(C= C3)O)OCCCN4CCCC4 | 1.2 | 13.99 | 4 | |

Figure 4B:
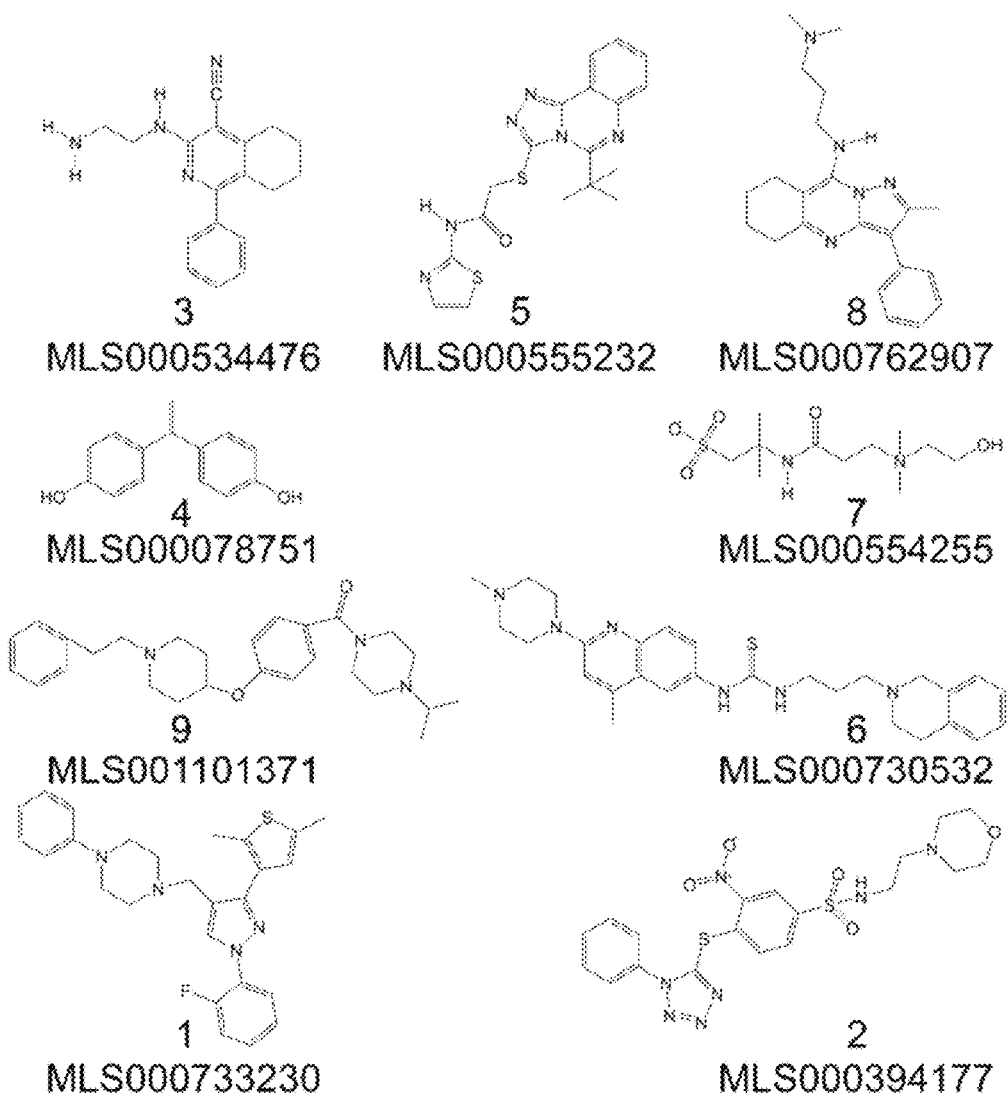
FIG. 4B is structural representation of the 9 numbered compounds indicated by their PubChem identification numbers.
Figure 6:
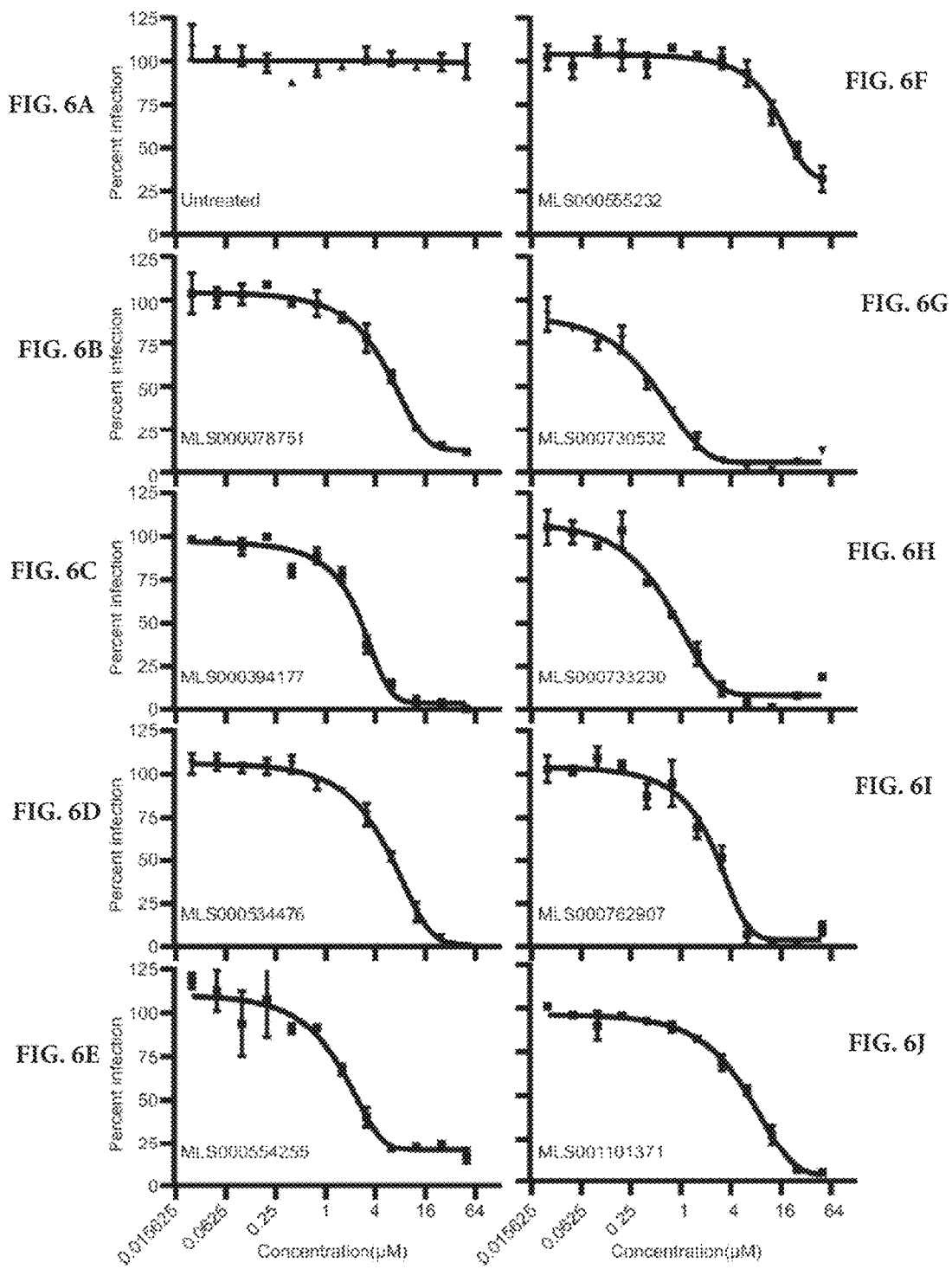
FIGS. 6A, 6B, 6C, 6D, 6E, 6F, 6G, 6H, 6I, and 6J are graphical representations of the dose dependent activity of compounds against EBOV-GFP in HeLa cells.

Interestingly, 42 of these 61 compounds also inhibited EBOV infection and in most cases were about 4-fold more potent over the concentration required to inhibit MARV infection. Of these, 17 yielded an $IC_{50}$ of less than 30 μM against both viruses. Nine of the compounds were readily available from an independent source and so could be verified for activity (TABLE 4 and FIG. 4B).

TABLE 4

| Compound name | MARV (Curve class) | HeLa IC50 (μM) | EBOV (curve class) | HeLa IC50 (μM) | Activity in macrophages IC50 (μM) |
|---|---|---|---|---|---|
| MLS000078751 | 1.5 | 6.1 | 1.3 | 25.6 | ~25 |
| MLS000394177 | 1.3 | 12.9 | 1.6 | 1.9 | 8.6 |
| MLS000534476 | 1.3 | 6.2 | 1.6 | 24.4 | 3.6 |
| MLS000554255 | 1.3 | 6.4 | 1.5 | 6.8 | 6.0 |
| MLS000555232 | 1.3 | 6.3 | 1.6 | 1.7 | 9.4 |
| MLS000730532 | 1.3 | 1.9 | 1.1 | 1.6 | 9.5 |
| MLS000733230 | 1.3 | 11.7 | 1.3 | 6.7 | 4.4 |
| MLS000762907 | 1.3 | 12.5 | 1.3 | 3.2 | 23.4 |
| MLS001101371 | 1.3 | 13.0 | 1.3 | 12.9 | 24.6 |

In each case the independently synthesized compound had activity within 1 μM to that seen using the MLSMR library as the source (FIGS. 5A, 5B, 5C, 5D. 5E, 5F, 5G, 5H, 5I and 5J, 6A, 6B, 6C, 6D, 6E, 6F, 6G, 6H, 6I and 6J and 7A, 7B, 7C, 7D, 7E, 7F, 7G, 7H, 7I and 7J). FIGS. 5A, 5B, 5C, 5D. 5E, 5F, 5G, 5H, 5I and 5J show the dose dependent activity of compounds against MARV in HeLa cells. HeLa cells were pretreated with twelve, half serial dilutions of compounds starting at 50 μM for 1 hour, in duplicates. Treated cells were infected with MARV at one day post-infection, and cells were immunostained using MARV specific antibody. MARV positive and total cell numbers were counted. A ratio of infected cell number to total cell number was used to determine percent infection. 6A, 6B, 6C, 6D, 6E, 6F, 6G, 6H, 6I and 6J show the dose dependent activity of compounds against EBOV-GFP in HeLa cells. HeLa cells were pretreated with twelve, half serial dilutions of compounds starting at 50 μM for 1 hour, in duplicates. Treated cells were infected with EBOV-GFP. GFP positive cells and total cell numbers were counted, 1 d after infection. A ratio of infected cell number to total cell number was used to determine percent infection. FIGS. 7A, 7B, 7C, 7D, 7E, 7F, 7G, 7H, 7I and 7J show the dose dependent activity of compounds against EBOV in HeLa cells. HeLa cells were pretreated with twelve, half serial dilutions of compounds starting at 50 μM for 1 hour, in duplicates. Treated cells were infected with EBOV. 1 d post infection cells were immunostained using EBOV specific antibody. EBOV positive and total cell numbers were counted. A ratio of infected cell number to total cell number was used to determine percent infection. It is likely that these pan Filovirus inhibitors were affecting cellular pathways shared by both viruses for entry. Additionally, all nine compounds inhibited EBOV infection in primary human macrophages which are a primary target of infection in vivo (TABLE 4, last column and FIGS. 8A, 8B, 8C, 8D, 8E, 8F, 8G, 8H, 8I, and 8J) suggesting potential for treating human infection. FIGS. 8A, 8B, 8C, 8D, 8E, 8F, 8G, 8H, 8I, and 8J show the dose dependent activity of compounds against EBOV in primary human macrophages. Human macrophages were differentiated from monocytes derived from human blood. Cells were pretreated with twelve, half serial dilutions of compounds starting at 50 μM for 1 hour, in duplicates. Treated cells were infected with EBOV. 1 d post infection cells were immunostained using EBOV specific antibody. EBOV positive and total cell numbers were counted. A ratio of infected cell number to total cell number was used to determine percent infection.

Entry was the most likely point at which compounds affected infection by the two pseudotypes and wild type viruses, since they all share the MARV or EBOV GPs and were affected with similar potency. So, to understand the mechanism of inhibition of virus entry, known steps of the virus entry pathway were examined using quantitative assays. Unfortunately, reagents against MARV are not as sensitive as those available for EBOV and the entry route of MARV is not as well characterized. For these reasons and since the compounds acted against both viruses, assays were focused on EBOV.

Example 5—MLS000078751 and MLS000534476 Inhibit Virus Binding to Cells

Figure 9A:
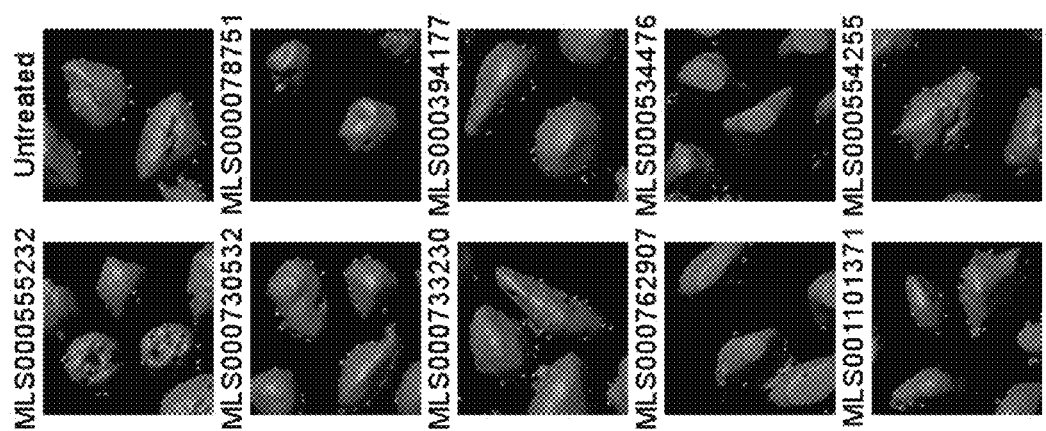
FIG. 9A is a series of images of HeLa cells stained using an EBOV GP specific antibody followed by Alexa546 labeled secondary antibody (red) to show Ebola viruses bound to cell surfaces. Cell bodies were stained using Cell Mask Blue.
Figure 9B:
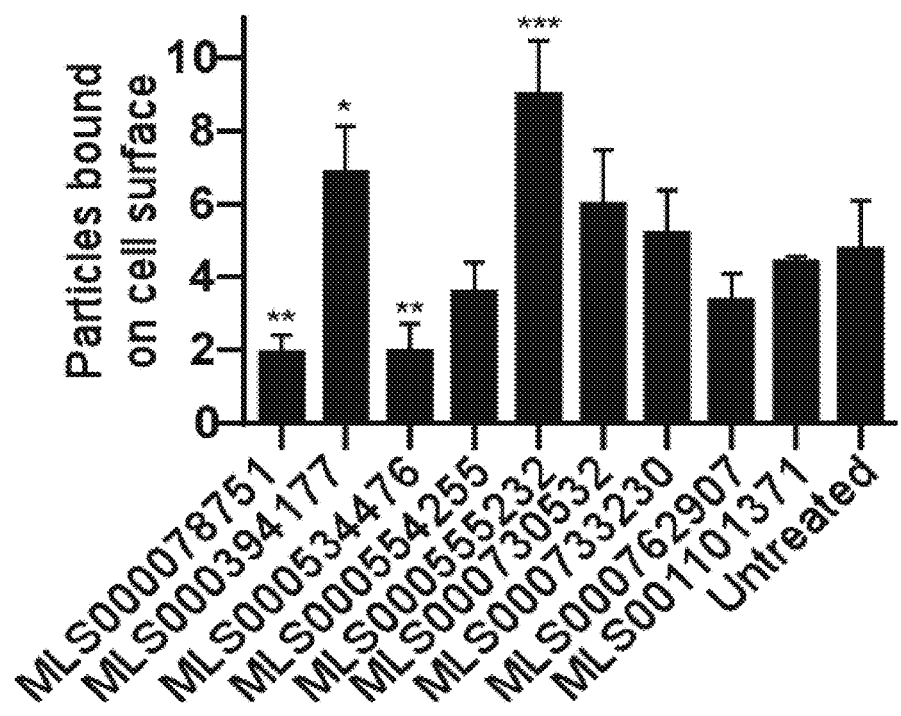
FIG. 9B is a graphical representation of the number of virus particles present on the cell surface after treatment.
Figure 9C:
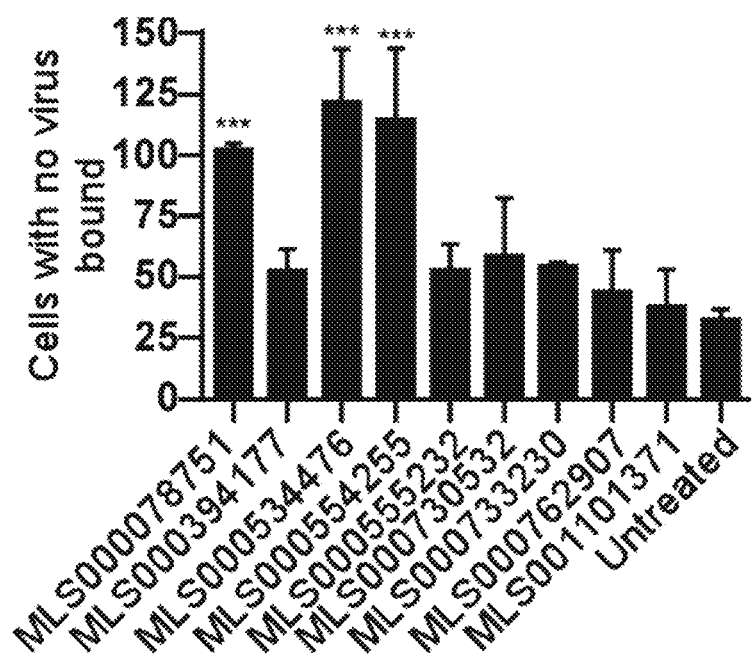
FIG. 9C is a graphical representation of the number of cells that had no virus bound and demonstrates compounds that prevent virus binding to cells.

The first step of virus entry into cells is binding to the cell surface. Virus particle binding was analyzed by counting the number of particles bound per cell as well as number of cells that had no virus attached. FIGS. 9A, 9B and 9C show the effect of compound treatment on binding of EBOV to cell surface. In FIG. 9A, HeLa cells were pre-treated with 50 μM of the indicated compound for 1 h and were then incubated with wild type EBOV for 2.5 h. The cells were then fixed and stained without permeabilization using an EBOV GP specific antibody followed by Alexa546 labeled secondary antibody (red). Cell bodies were stained using Cell Mask Blue. 3D modeling of deconvolved image z-stacks was done using Imaris software. In FIG. 9B, the number of virus particles present on the cell surface were counted. Only MLS000078751 and MLS000534476 significantly decreased the total viral particles bound by 53% and 55% respectively (FIGS. 9A and 9B). Both compounds also reduced particle uptake. This was measured by counting total particles associated with cells per field as well as the number of cells lacking virus particles inside (FIG. 9C). In FIG. 9C, a second analysis of the number of cells that had no virus bound was also performed. Data are the average of at least 100 cells+/−st. dev. All assays were performed 3 times with similar outcomes (*$P<0.05$, $P<0.01$ and *$P<0.001$). Of the remaining 7 compounds, none significantly decreased particle binding and only MLS000554255 increased the number of cells without virus bound. Surprisingly, MLS000394177 and MLS000555232 enhanced virus interaction with cells by 44% and 89% respectively. This suggests that each may cause virus to accumulate on the cell surface and not be internalized.

Figure 10:
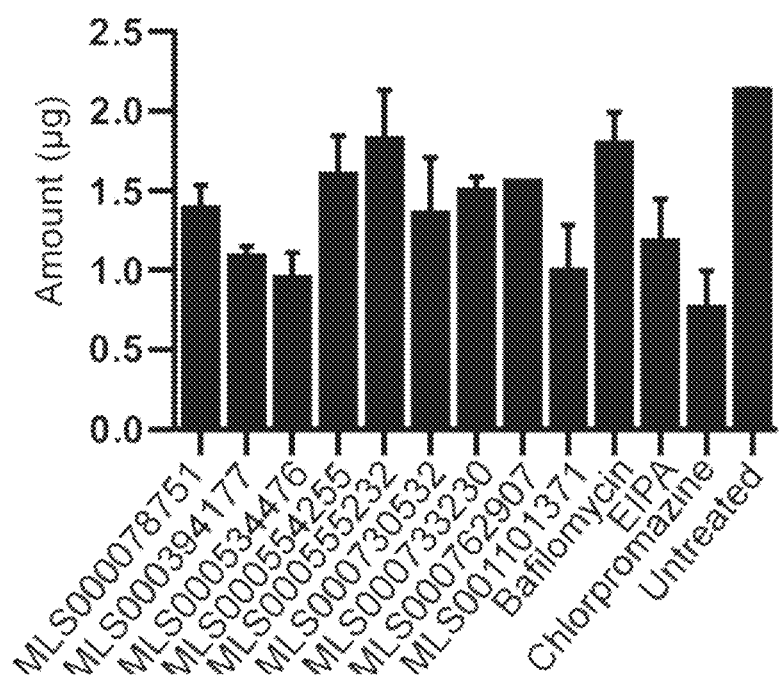
FIG. 10 is a graphical representation of the effect of compound treatment on amount of binding of transferrin to cells.

To determine if the inhibition of virus binding was specific for EBOV or a generalized disruption of ligand-receptor interaction, binding of transferrin to cells was measured. FIG. 10 shows effect of compound treatment on binding of transferrin to cells. HeLa cells were serum starved for 4 hours followed by treatment with compounds in triplicates for 1 hour in serum free medium. Treated cells were then transferred to 14° C. Cells were incubated with 25 μg/ml of human transferrin for 40 minutes followed by washing and lysis. Transferrin bound to cells was estimated using ELISA. Bafilomycin A (10 nM) an inhibitor of endosomal acidification, EIPA (25 μM) a specific inhibitor of macropinocytosis and Chlorpromazine (25 μM) an inhibitor of clathrin mediated endocytosis and known to block transferrin uptake were used as controls. All assays were performed 3 times with similar outcomes. Six of the compounds had no significant effect on transferrin binding while the remaining 3 compounds reduced binding but by no more than 2-fold. MLS000534476 resulted in the greatest decrease in transferrin binding to cells by >55%. It is therefore likely that MLS000534476 acts non-specifically to block virus and transferrin binding to cellular receptors. In contrast, MLS000078751 appears to inhibit Filovirus entry by specifically, reducing virus-cell interaction. The remaining 7 compounds were investigated further for defects in virus uptake.

Example 6—Inhibition of Macropinocytic Uptake

Figure 11A:
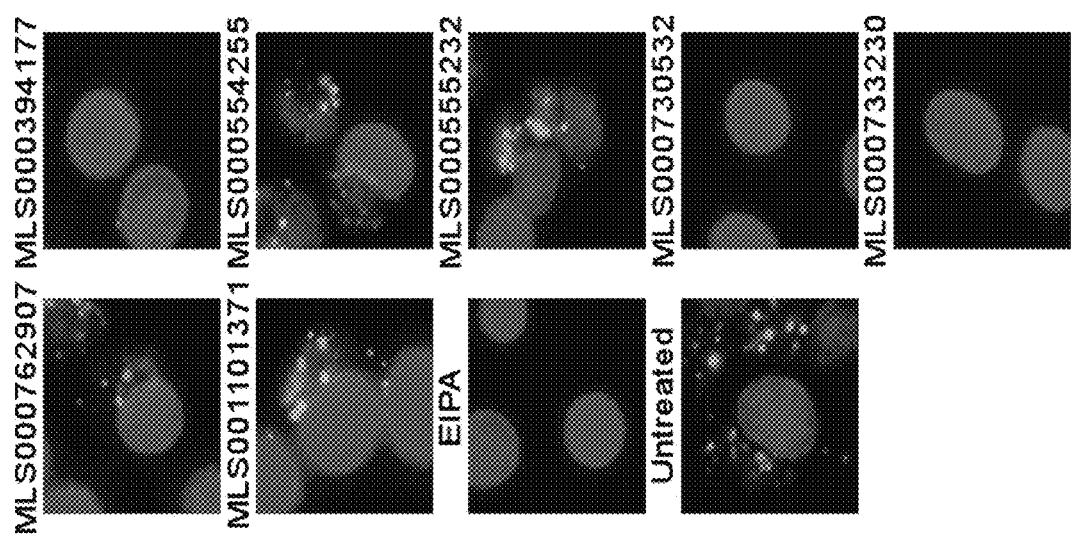
FIGS. 11A, 11B, 11C, 11D, 11E, and 11F demonstrate the effect of compound treatment on macropinocytosis and uptake of EBOV into cells.
Figure 11B:
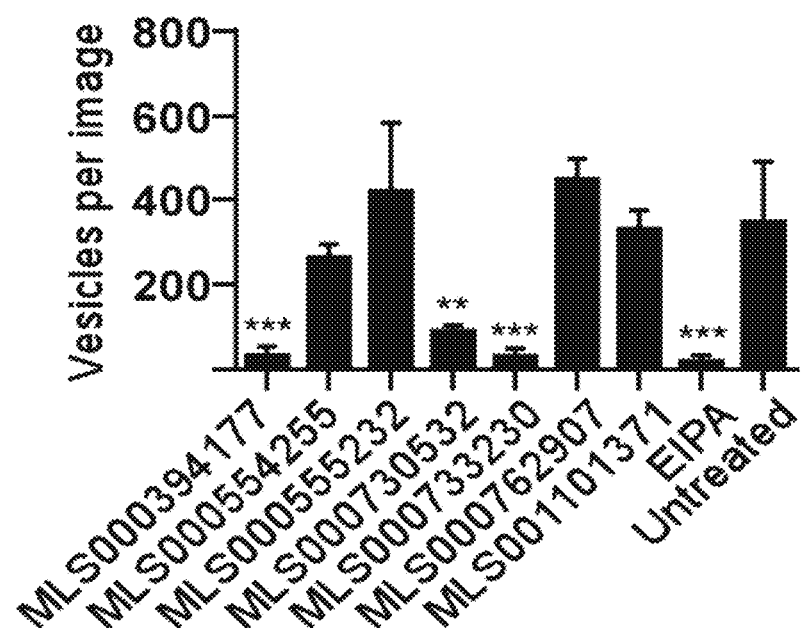
Figure 11C:
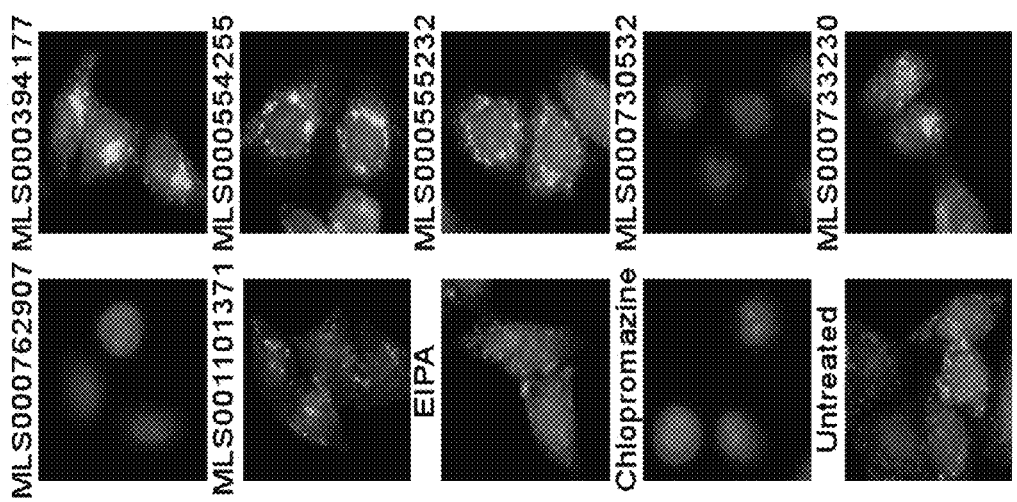
Figure 11D:
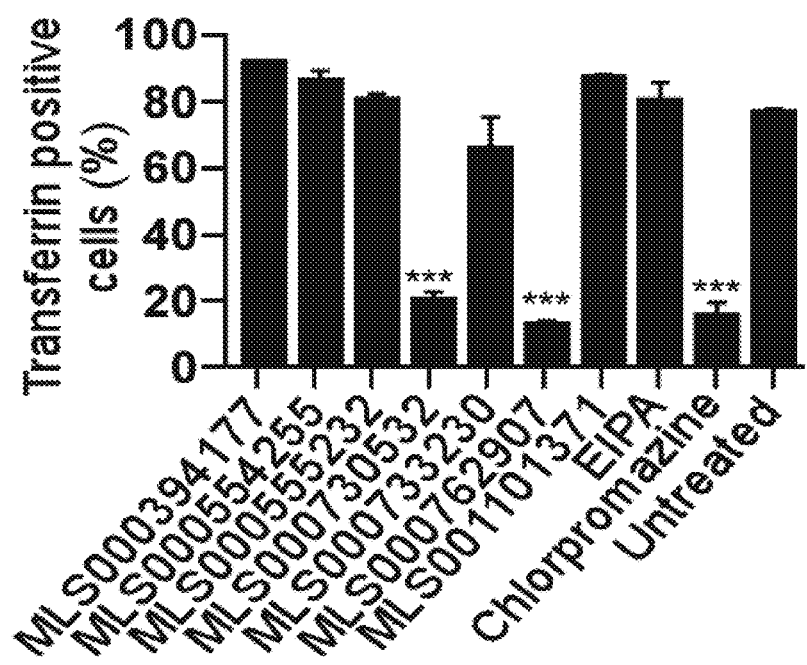
Figure 11E:
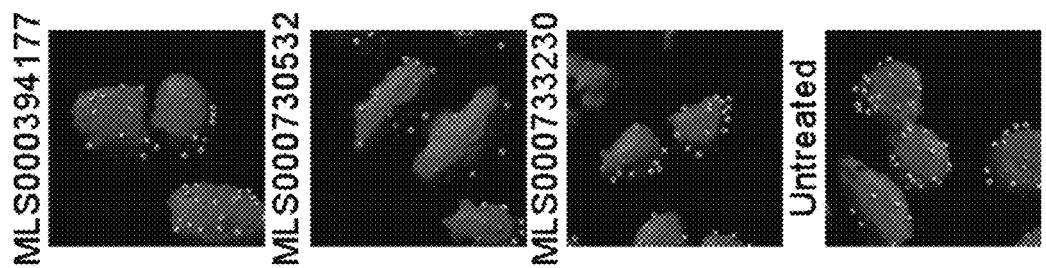
Figure 11F:
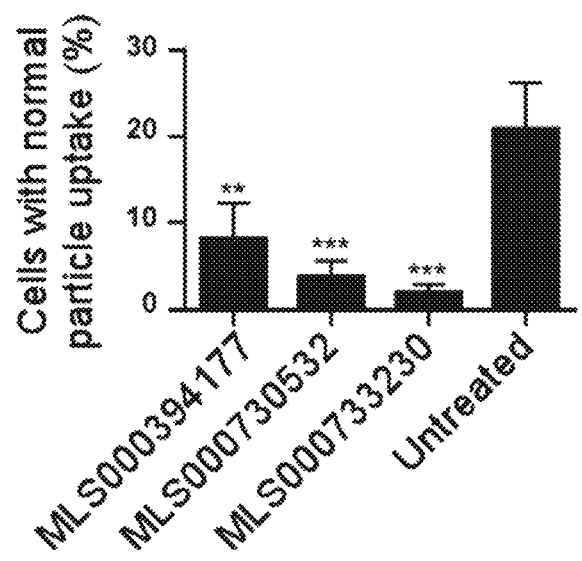

EBOV predominantly uses macropinocytosis for productive uptake into cells. High molecular weight dextran is commonly used as a marker of macropinocytic uptake and is strongly associated with EBOV particles after uptake. MLS000394177, MLS000730532 and MLS000733230 were found to reduce the uptake of fluorescently labeled dextran (FIG. 11A) by approximately 91%, 74% and 91% respectively (FIG. 11B). As a control, EIPA, a commonly accepted inhibitor of macropinocytosis was used and produced similar inhibition of dextran uptake (95%). MLS000394177, MLS000730532 and MLS000733230 also reduced the number of viral particles inside the cell body by 62%, 89% and 91% respectively (FIGS. 11E and 11F).

As a measure of specificity, and to control for a generalized disruption of membrane function and endocytic uptake, transferrin uptake, a well characterized marker of clathrin-mediated endocytosis, was measured. Both MLS000394177 and MLS000733230 had no effect on transferrin uptake. In contrast, MLS000730532 impaired uptake of this marker, comparable to chlorpromazine, a known inhibitor of clathrin-mediated endosome trafficking (FIGS. 11C and 11D). Similarly, MLS00076907 also inhibited transferrin uptake.

Since MLS000394177 and MLS000733230 inhibit EBOV and dextran uptake but did not affect virus binding to cells or transferrin uptake, each appears to specifically inhibit Filovirus entry by affecting macropinocytosis, similarly to EIPA, while MLS000730532 appears to cause a more generalized disruption of endocytosis. The remaining 4 compounds that did not affect macropinocytosis (including MLS000762907) were then tested for impact on trafficking of EBOV VLPs beyond the macropinosome to early endosomes (colocalized with EEA1) and then late endosomes (colocalized with LAMP1).

Figure 12A:
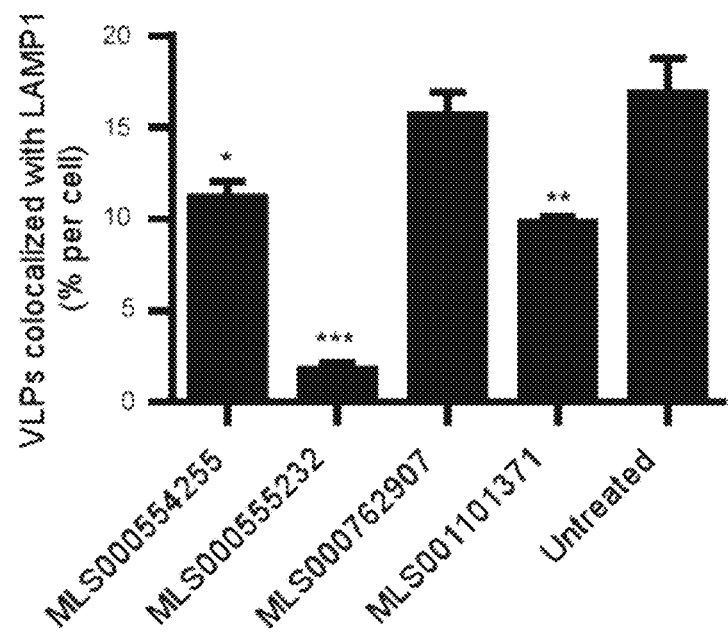
FIGS. 12A and 12B are graphical representations of the effect of treatment on virus-like particle (VLP) trafficking. VLPs are used as a surrogate for virus for this type of study as they give a strong signal inside the cell.
Figure 12B:
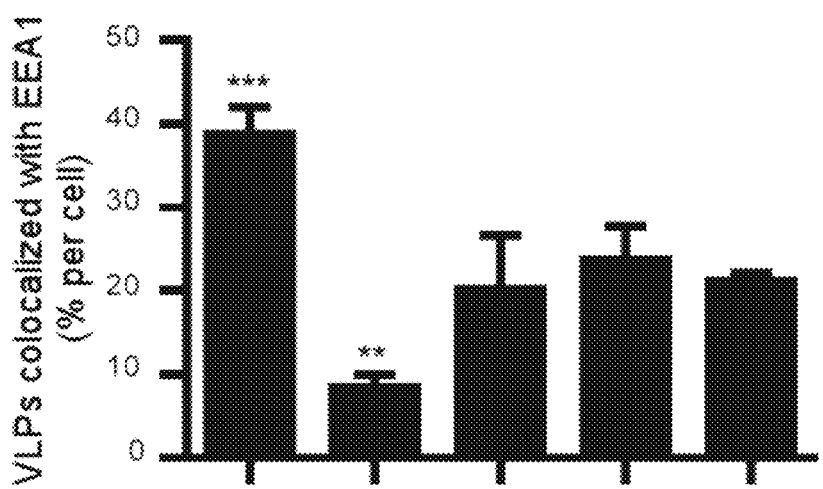

Example 7—Effect of Compounds on Colocalization of EBOV VLPs to EEA1 and LAMP1-Positive Compartments After macropinocytic uptake, virus is trafficked through the endosomal network, during which the GP is cleaved by endosomal proteases. Virus-like particles (VLPs) tagged using GFP-VP40 were used to follow trafficking since the GFP is encapsulated by the viral membrane. It should therefore resist degradation by the endosomal proteases. After treatment with MLS000762907 and MLS001101371, VLPs colocalized with EEA1 positive vesicles normally. In contrast, MLS000555232 reduced colocalization of EBOV VLPs with EEA1-positive vesicles by 77%, while MLS000554255 increased colocalization of VLPs with EEA1-positive vesicles by 83% (FIG. 12A). When LAMP1 association was tested, MLS000554255, MLS000555232, and MLS001101371 reduced the number of VLPs present in LAMP1-positive vesicles significantly ($P<0.05$) by 33%, 89%, and 41% respectively (FIG. 12B). Taken together, MLS000555232 appears to block colocalization to EEA1 positive and LAMP1 positive vesicles, whereas MLS000554255 and MLS001101371 impair colocalization with LAMP1 positive vesicles only. Of these, MLS000555232 also shows nearly 2-fold increase in virus particle binding to the cell surface (FIG. 9B); suggesting that this compound may alter receptor and virus trafficking from the cell surface. Only MLS000762907 had no effect on VLP colocalization with EEA1 and LAMP1 vesicles. As above, MLS000762907 reduced uptake of transferrin but not of dextran (FIGS. 11C and 11D) or virus. Together, these observations suggest that MLS000762907 may interfere with trafficking (via clathrin-mediated uptake) of an unidentified cofactor that interacts with virus after uptake into cells.

Of the 9 compounds evaluated, 2 appear to block virus binding to cells, 3 block macropinocytic uptake and 4 alter endocytic trafficking of virus particles in cells (Table 5). Each inhibit both EBOV and MARV infection of cells, are not toxic at up to 50 µM and so are promising candidates for development as therapeutic agents.

TABLE 5

Summary of assay outcomes used to determine the mechanism of action for the indicated compounds against EBOV infection.

| Compound Name | Surface interaction | Uninfected cell number | Dextran Uptake | Transferrin binding | Transferrin uptake | Effect on EEA1 | Effect on LAMP1 | Acidification Block | Cathepsin cleavage | NPC1 C-loop binding | Mechanism of action |
|---|---|---|---|---|---|---|---|---|---|---|---|
| MLS000078751 | − | + | 0 | | 0 | | | − | 0 | 0 | Surface interaction block |
| MLS000394177 | + | 0 | − | | 0 | | | + | 0 | 0 | Macropinocytosis block |
| MLS000534476 | − | + | 0 | | − | | | + | 0 | 0 | Surface interaction block |
| MLS000554255 | 0 | + | 0 | | 0 | + | − | − | 0 | 0 | Late endocytic trafficking block |
| MLS000555232 | + | 0 | 0 | | 0 | − | − | − | 0 | 0 | Early endocytic trafficking block |
| MLS000730532 | 0 | 0 | − | | − | | | + | 0 | 0 | Uptake block |
| MLS000733230 | 0 | 0 | − | | 0 | | | + | 0 | 0 | Macropinocytosis block |
| MLS000762907 | 0 | 0 | 0 | | − | 0 | 0 | + | 0 | 0 | Trafficking block |
| MLS001101371 | 0 | 0 | 0 | | 0 | 0 | − | + | 0 | 0 | Late endocytic trafficking bloc |

0 indicates no effect, + indicates increase in assay activity, − indicates decrease in assay activity.

Those skilled in the art will recognize, or be able to ascertain using no more than routine experimentation, many equivalents to the specific embodiments described herein. Such equivalents are intended to be encompassed by the following claims.

The invention claimed is:

1. A method for treating or preventing an infection in a subject, the method comprising administering to the subject a therapeutically effective amount of a pharmaceutical composition having the general formula (I) or a pharmaceutically acceptable salt thereof, wherein the infection is an Ebolavirus infection or a Marburgvirus infection:

General formula (I)

2. A method for treating or preventing an infection in a subject, the method comprising administering to the subject a therapeutically effective amount of a pharmaceutical composition having the general formula (II) or a pharmaceutically acceptable salt thereof, wherein the infection is an Ebolavirus infection or a Marburgvirus infection:

General formula (II)

* * * * *